United States Patent
Kesteleyn et al.

(10) Patent No.: US 9,944,598 B2
(45) Date of Patent: Apr. 17, 2018

(54) MONO- OR DI-SUBSTITUTED INDOLE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Berlare (BE); Jean-François Bonfanti, Ande (FR); Tim Hugo Maria Jonckers, Heist-op-den-Berg (BE); Pierre Jean-Marie Bernard Raboisson, Rosieres (BE); Dorothée Alice Marie-Eve Bardiot, Heverlee (BE); Arnaud Didier M Marchand, Bierbeek (BE)

(73) Assignees: Janssen Pharmaceuticals, Inc., Titusville, NJ (US); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 15/515,574

(22) PCT Filed: Sep. 30, 2015

(86) PCT No.: PCT/EP2015/072551
§ 371 (c)(1),
(2) Date: Mar. 29, 2017

(87) PCT Pub. No.: WO2016/050841
PCT Pub. Date: Apr. 7, 2016

(65) Prior Publication Data
US 2017/0298017 A1  Oct. 19, 2017

(30) Foreign Application Priority Data

Oct. 1, 2014 (EP) .................................... 14187374
Mar. 16, 2015 (EP) .................................... 15159164

(51) Int. Cl.
*C07D 209/14* (2006.01)
*A61K 31/404* (2006.01)

(52) U.S. Cl.
CPC .......... *C07D 209/14* (2013.01); *A61K 31/404* (2013.01)

(58) Field of Classification Search
CPC .................................................... C07D 209/14
See application file for complete search history.

(56) References Cited

FOREIGN PATENT DOCUMENTS

WO 2013/045516 4/2013

OTHER PUBLICATIONS

International Search Report and Written Opinion dated Oct. 28, 2015, for Corresponding International Application PCT/EP2015/072551.

*Primary Examiner* — Laura L. Stockton
(74) *Attorney, Agent, or Firm* — Andrea Jo Kamage

(57) ABSTRACT

The present invention concerns mono- or di-substituted indole derivatives (I) which are useful to prevent or treat dengue viral infections and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

(I)

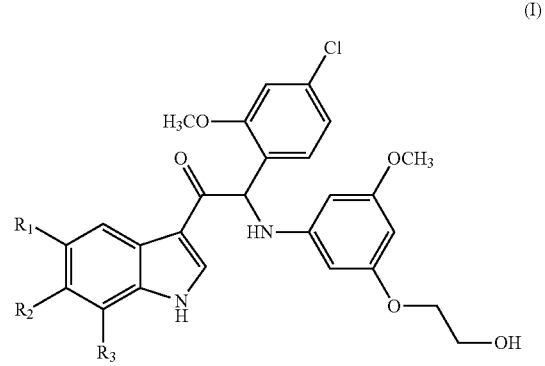

17 Claims, No Drawings

SEQUENCE LISTING

<160> NUMBER OF SEQ ID NOS: 14

<210> SEQ ID NO 1
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
    /mol_type="unassigned DNA"

<400> SEQUENCE: 1
tcggagccgg agtttacaaa                                        20

```
<210> SEQ ID NO 2
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 2
tcttaacgtc cgcccatgat                                              20

<210> SEQ ID NO 3
<211> LENGTH: 19
<212> TYPE: DNA
<213> ORGANISM: Dengue virus
<220> FEATURE:
<221> NAME/KEY: source
<222> LOCATION: 1..19
<223> OTHER INFORMATION: /organism="Dengue virus"
      /mol_type="unassigned DNA"

<400> SEQUENCE: 3
attccacaca atgtggcat                                               19

<210> SEQ ID NO 4
<211> LENGTH: 23
<212> TYPE: DNA
<213> ORGANISM: Dengue virus
<220> FEATURE:
<221> NAME/KEY: source
<222> LOCATION: 1..23
<223> OTHER INFORMATION: /organism="Dengue virus"
      /mol_type="unassigned DNA"

<400> SEQUENCE: 4
ggatagacca gagatcctgc tgt                                          23

<210> SEQ ID NO 5
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 5
cattccattt tctggcgttc                                              20

<210> SEQ ID NO 6
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 6
caatccatct tgcggcgctc                                              20

<210> SEQ ID NO 7
<211> LENGTH: 20
```

```
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 7
cagcatcatt ccaggcacag                                              20

<210> SEQ ID NO 8
<211> LENGTH: 20
<212> TYPE: DNA
<213> ORGANISM: Dengue virus
<220> FEATURE:
<221> NAME/KEY: source
<222> LOCATION: 1..20
<223> OTHER INFORMATION: /organism="Dengue virus"
      /mol_type="unassigned DNA"

<400> SEQUENCE: 8
caacatcaat ccaggcacag                                              20

<210> SEQ ID NO 9
<211> LENGTH: 19
<212> TYPE: DNA
<213> ORGANISM: Dengue virus
<220> FEATURE:
<221> NAME/KEY: source
<222> LOCATION: 1..19
<223> OTHER INFORMATION: /organism="Dengue virus"
      /mol_type="unassigned DNA"

<400> SEQUENCE: 9
cggttagagg agacccctc                                               19

<210> SEQ ID NO 10
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 10
gagacagcag gatctctggt c                                            21

<210> SEQ ID NO 11
<211> LENGTH: 28
<212> TYPE: DNA
<213> ORGANISM: Dengue virus
<220> FEATURE:
<221> NAME/KEY: source
<222> LOCATION: 1..28
<223> OTHER INFORMATION: /organism="Dengue virus"
      /mol_type="unassigned DNA"

<400> SEQUENCE: 11
aaggactaga ggttagagga gaccccccc                                    28

<210> SEQ ID NO 12
<211> LENGTH: 18
<212> TYPE: DNA
<213> ORGANISM: Dengue virus
<220> FEATURE:
<221> NAME/KEY: source
```

```
<222> LOCATION: 1..18
<223> OTHER INFORMATION: /organism="Dengue virus"
      /mol_type="unassigned DNA"

<400> SEQUENCE: 12
ggccaggtca tcaccatt                                                 18

<210> SEQ ID NO 13
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 13
atgtccacgt cacacttcat g                                             21

<210> SEQ ID NO 14
<211> LENGTH: 21
<212> TYPE: DNA
<213> ORGANISM: Dengue virus
<220> FEATURE:
<221> NAME/KEY: source
<222> LOCATION: 1..21
<223> OTHER INFORMATION: /organism="Dengue virus"
      /mol_type="unassigned DNA"

<400> SEQUENCE: 14
ttccgctgcc ctgaggctct c                                             21
```

MONO- OR DI-SUBSTITUTED INDOLE DERIVATIVES AS DENGUE VIRAL REPLICATION INHIBITORS

This application is a 35 U.S.C. § 371 nationalization of PCT application PCT/EP2015/072551 filed Sept. 30, 2015, which claims priority to European patent application 14187374.5 Oct. 1, 2014 and European patent application 15159164.1 filed Mar. 16,2015, all of which are incorporated herein by reference.

The present invention relates to mono- or di-substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control the disease associated with dengue viral infection, the only available methods at present are mosquito eradication strategies to control the vector. Although progress is being made in the development of vaccines against dengue, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Despite large efforts over the past 3 decades, there is currently no vaccine available to protect humans against dengue virus disease. The main problem is to develop a vaccine that offers protection against all four serotypes (a tetravalent vaccine) to the same extent. Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

The present invention now provides compounds, mono- or di-substituted indole derivatives, which show high potent activity against all four (4) serotypes of the Dengue virus. Also the compounds according to the invention possess a good pharmacokinetic profile and surprisingly these specific compounds show an improved chiral stability.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration an effective amount of one or more such compounds, or a pharmaceutically acceptable salt thereof optionally in combination with one or more other medicines, like another antiviral agent, to a patient in need thereof.

One aspect of the invention is the provision of compounds of formula (I)

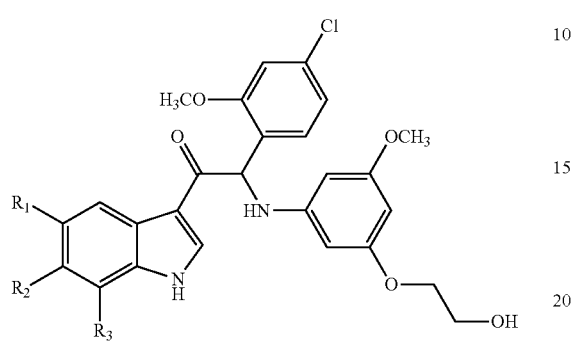

a stereo-isomeric form, a pharmaceutically acceptable salt, solvate or polymorph thereof comprising a mono- or di-substituted indole group;

said compound is selected from the group wherein:

$R_1$ is H, $R_2$ is F and $R_3$ is H, F or $CH_3$;
$R_1$ is F or $CH_3$, $R_2$ is $OCH_3$ and $R_3$ is H;
$R_1$ is F, $R_2$ is H and $R_3$ is $CH_3$;
$R_1$ is H, $R_2$ is $OCH_3$ and $R_3$ is H;
$R_1$ is H, $R_2$ is Cl and $R_3$ is H or $CH_3$;
$R_1$ is F, $R_2$ is F and $R_3$ is H or
$R_1$ is $CH_3$, $R_2$ is H and $R_3$ is F.

In particular the compounds of the invention or their stereo-isomeric form, a pharmaceutically acceptable salt, solvate or polymorph thereof are selected from the group:

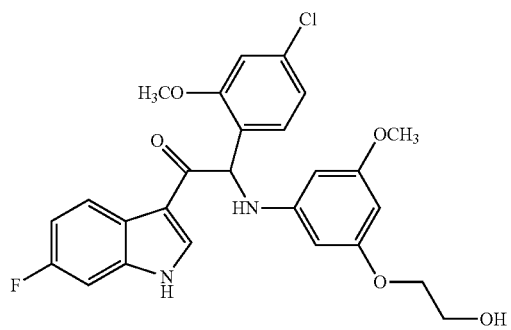

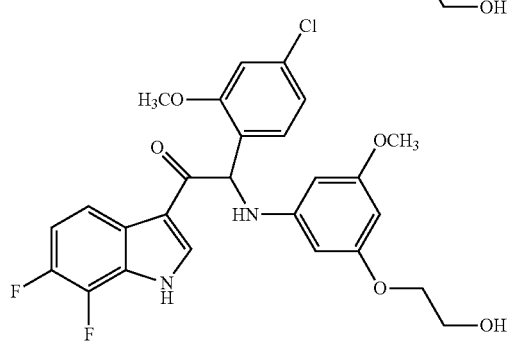

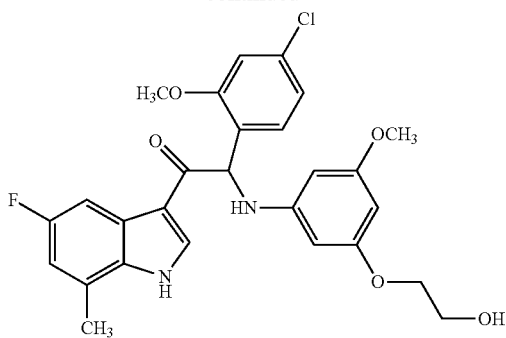

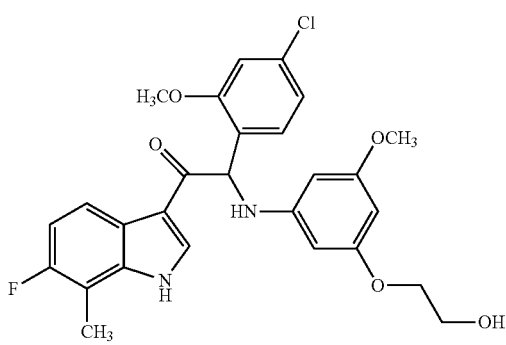

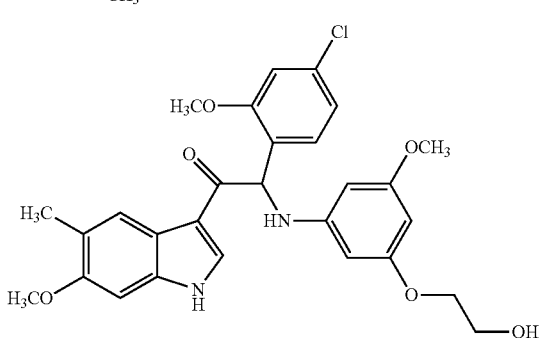

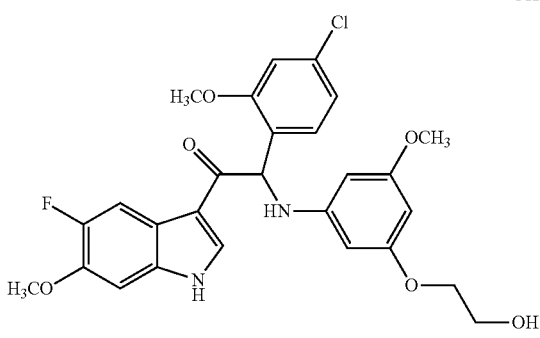

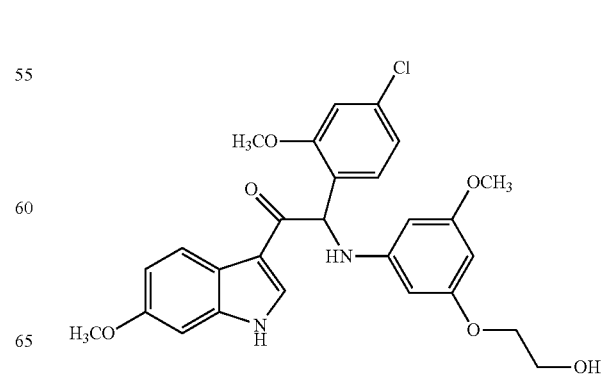

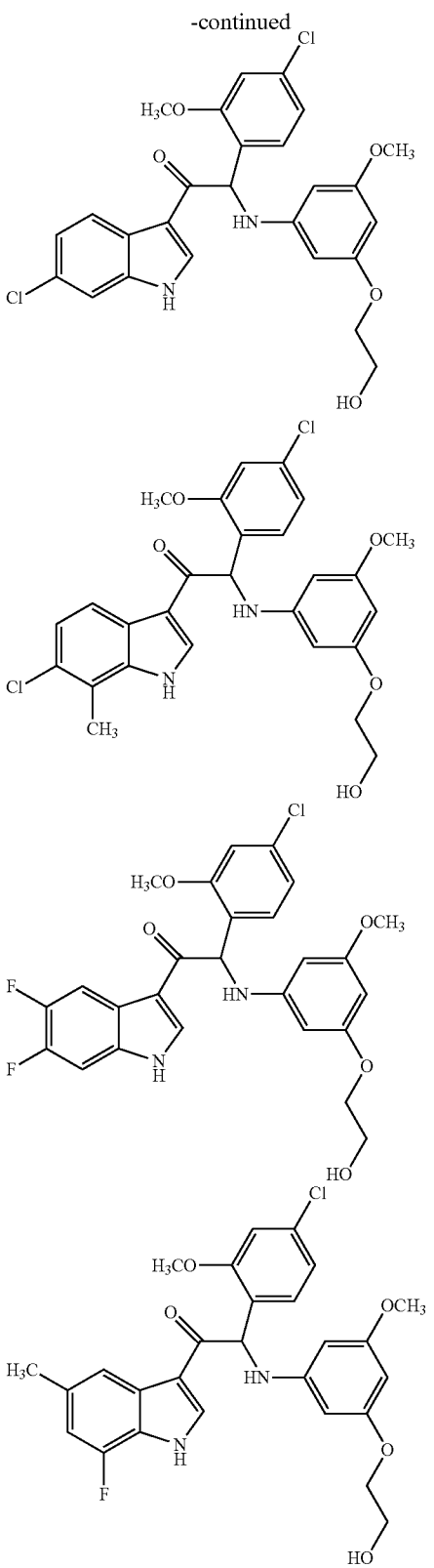

Part of the current invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14. The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all dia-stereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

General Synthetic Approaches

The synthesis of compounds of general formula I can be performed as outlined in Scheme 1: 2-(4-chloro-2-methoxyphenyl)acetic acid (II) can be converted to the corresponding 2-(4-chloro-2-methoxyphenyl)acetyl chloride (III) with a chlorination reagent like for example thionyl chloride. The Friedel-Crafts reaction of the acid chloride III with a substituted indole of general formula IV can be performed using a Lewis acid reagent like for example $Et_2AlCl$ in a suitable solvent like for example $CH_2Cl_2$, and under suitable reaction conditions that typically involve cooling, to provide the 3-acylated indole of general formula V. The introduction of an aniline moiety in alpha position to the carbonyl moiety of the compounds of general formula V can be accomplished by a reaction sequence that involves for example bromination of V with a reagent like for example phenyltrimethylammonium tribromide in a suitable solvent like for example THF, to provide the compounds of general formula VI, and subsequent reaction of the compounds of general formula VI with 2-(3-amino-5-methoxyphenoxy)ethanol (VII) in a suitable solvent like for example $CH_3CN$, and typically using a base like for example TEA or DIPEA, to provide the compounds of general formula I as racemic mixtures. Chiral separation of the compounds of general formula I can be performed by for example chiral chromatography to provide the Enantiomers A and B of general formula I.

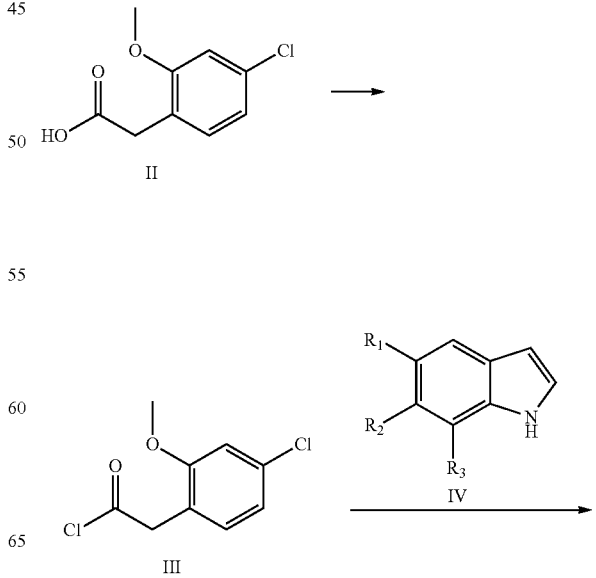

Scheme 1

-continued

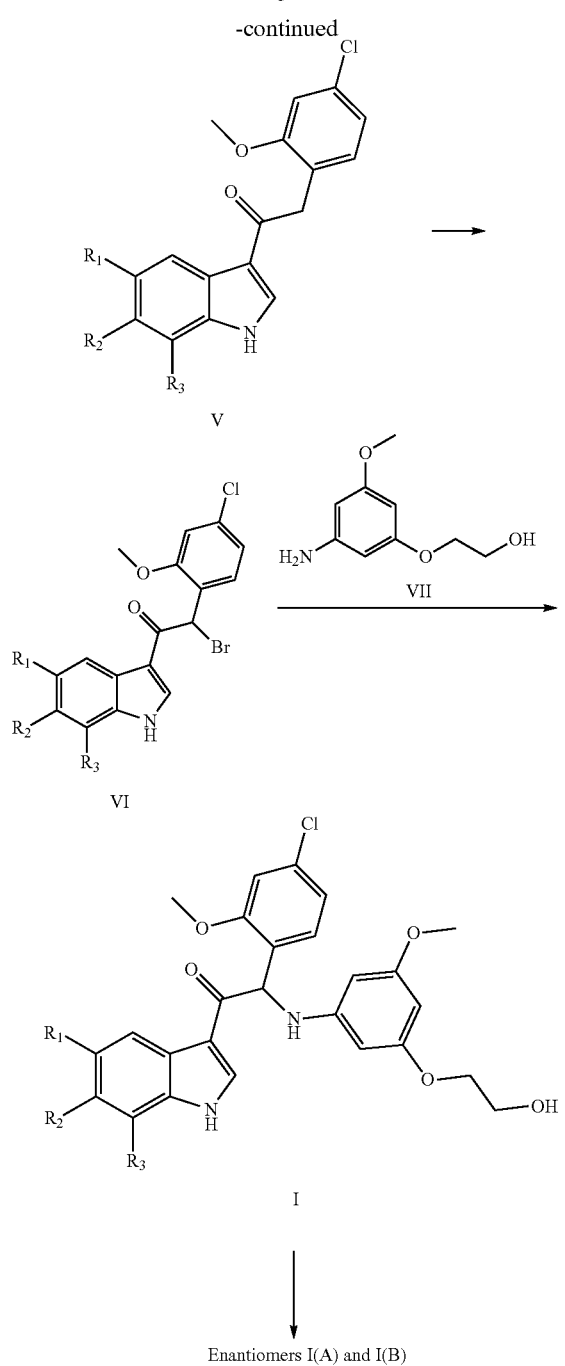

As an alternative approach, the intermediate of general formula V can also be prepared as outlined in Scheme 2: The N-Boc-protected substituted indole-3-carbaldehyde of general formula VIII can be converted to the corresponding Strecker-type of intermediate of general formula IX by reaction with morpholine in the presence of reagents like for example sodium cyanide and sodium bisulfite and in a suitable solvent like for example a mixture of water and a water-mixable organic solvent like for example dioxane. Alkylation of the compound of general formula IX with 4-chloro-2-methoxy-benzylchloride can be accomplished in the presence of a base like for example potassium hexamethyldisilazane and in a suitable solvent like for example DMF to provide the compound of general formula X.

Submission of the compound of general formula X to a suitable aqueous acidic hydrolytic condition like for example treatment with an aqueous hydrochloric acid solution at elevated temperature, provides the intermediate of general formula V.

Scheme 2

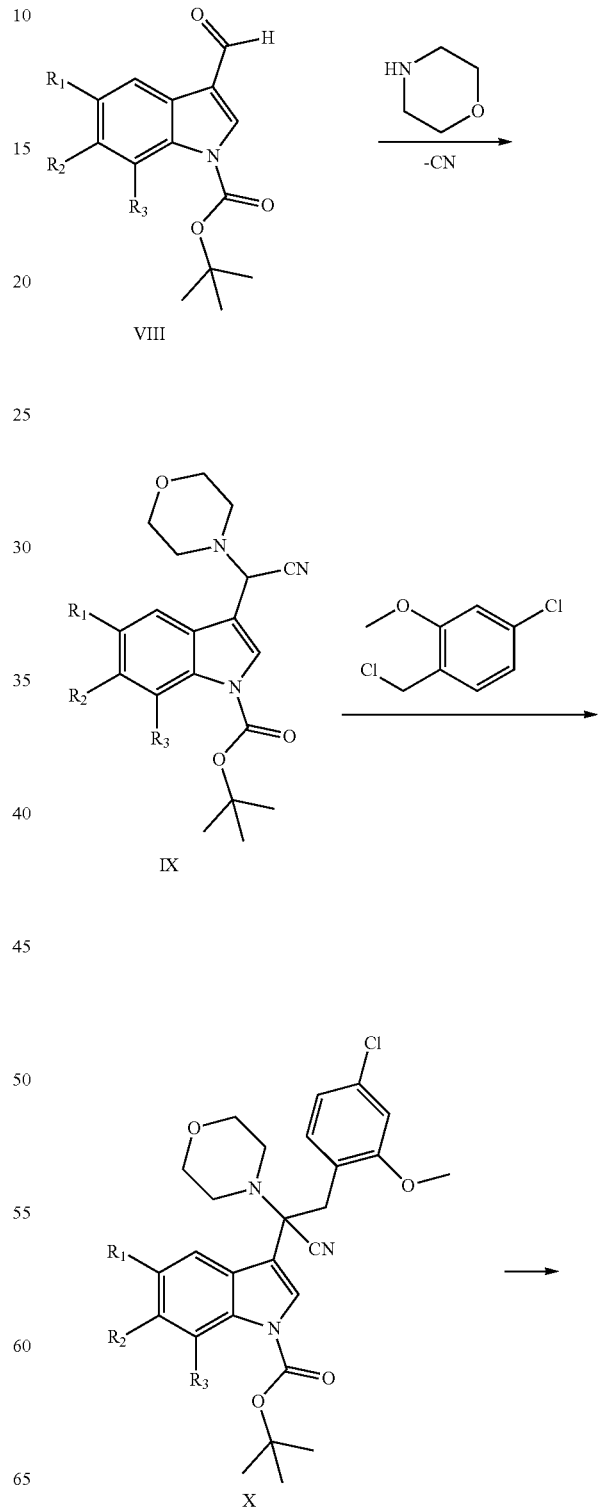

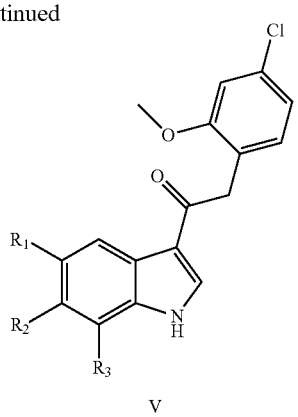

V

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LC/MS Method codes (Flow expressed in mL/min; column temperature (T) in ° C.; Run time in minutes)

| Method code | Instrument | Column | Mobile phase | Gradient | Flow Col T | Run time (min) |
|---|---|---|---|---|---|---|
| LC-A | Waters: Acquity ® UPLC ® - DAD-SQD | Waters: BEH C18 (1.7 μm, 2.1 × 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8 mL/min 55° C. | 2 |
| LC-B | Waters: Acquity ® UPLC ® - DAD-SQD | Waters: HSS T3 (1.8 μm, 2.1 × 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min 55° C. | 3.5 |
| LC-C | Waters: Acquity ® UPLC ® - DAD-Quattro Micro ™ | Waters: BEH C18 (1.7 μm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min. | 0.343 mL/min 40° C. | 6.2 |
| LC-D | Waters: Acquity ® UPLC ® - DAD-TQD | Waters: HSS C18 (1.8 μm, 2.1 × 50 mm | A: 0.1% Formic acid in $H_2O$ B: $CH_3CN$ | 50% A to 10% in 3.5 min, held for 1.5 min. | 0.5 mL/min 40° C. | 5 |

SFC-MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars.

If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars.

| Method code | column | mobile phase | gradient | Flow Col T | Run time BPR |
|---|---|---|---|---|---|
| SFC-A | Daicel Chiralpak ® AD-H column (5 μm, 150 × 4.6 mm) | A: $CO_2$<br>B: MeOH | 30% B hold 7 min, | 3<br>35 | 7<br>100 |
| SFC-B | Daicel Chiralpak ® AD-H column (5 μm, 150 × 4.6 mm) | A: $CO_2$<br>B: MeOH | 40% B hold 7 min, | 3<br>35 | 7<br>100 |
| SFC-C | Daicel Chiralcel ® OJ-H column (5 μm, 250 × 4.6 mm) | A: $CO_2$<br>B: MeOH | 40% B hold 7 min, | 3<br>35 | 7<br>100 |
| SFC-D | Daicel Chiralcel ® OD-H column (5 μm, 150 × 4.6 mm) | A: $CO_2$<br>B: MeOH | 40% B hold 7 min, | 3<br>35 | 7<br>100 |
| SFC-E | WHELK-O1 (S,S) 250 * 4.6 mm 5 μm Regis | A: $CO_2$<br>B: MeOH | 60% B hold 7 min, | 3<br>35 | 7<br>100 |
| SFC-F | Daicel Chiralpak ® AS3 column (3.0 μm, 150 × 4.6 mm) | A: $CO_2$<br>B: EtOH + 0.2% iPrNH$_2$ + 3% H$_2$O | 25% B hold 6 min, to 50% in 1 min hold 2.5 min | 2.5<br>40 | 9.5<br>110 |
| SFC-G | Daicel Chiralpak ® AS3 column (3.0 μm, 150 × 4.6 mm) | A: $CO_2$<br>B: EtOH + 0.2% iPrNH$_2$ + 3% H$_2$O | 30% B hold 6 min, to 50% in 1 min hold 2.5 min | 2.5<br>40 | 9.5<br>110 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations:

Optical rotations were measured on a Perkin-Elmer 341 polarimeter with a sodium lamp and reported as follows: [α]° (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1

Synthesis of 2-(4-chloro-2-methoxyphenyl)-1-(6-fluoro-1H-indol-3-yl)-2-((3-(2-hydroxyethoxy)-5-methoxyphenyl)amino)ethanone (Compound 1) and Chiral Separation into Enantiomers 1A and 1B

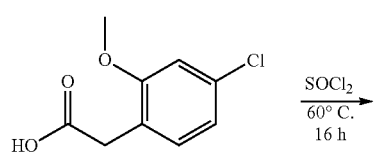

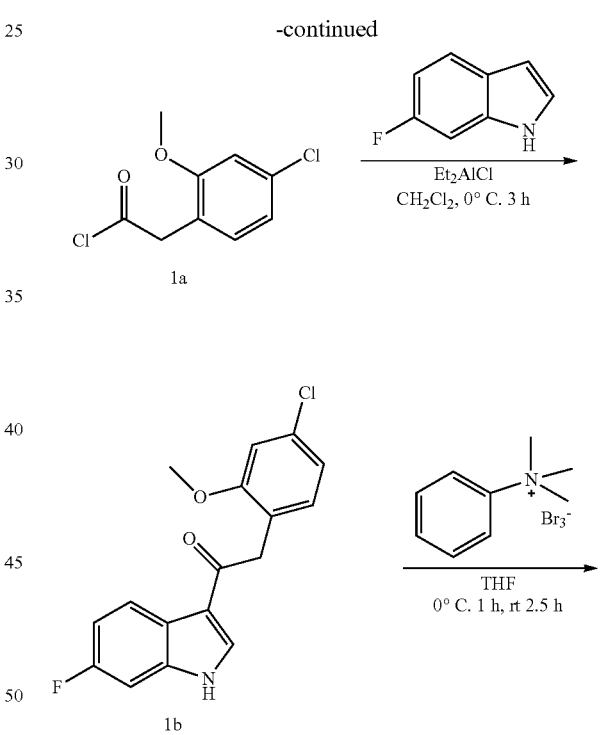

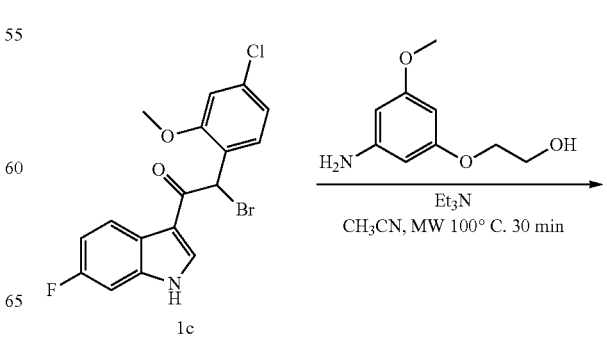

-continued

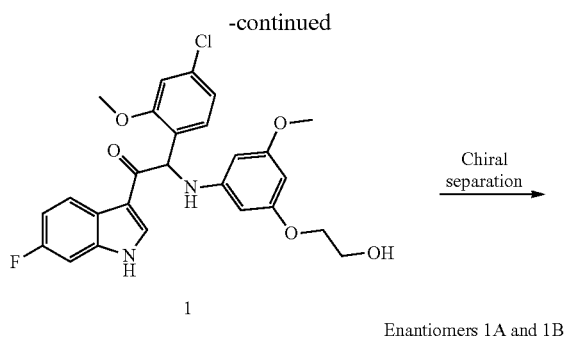

Chiral separation

Enantiomers 1A and 1B

Synthesis of Intermediate 1a:

2-(4-Chloro-2-methoxyphenyl)acetic acid [CAS 170737-95-8] (5.8 g, 28.9 mmol) was added in small portions to thionyl chloride (50 mL) and the resulting solution was stirred overnight at 60° C. The solvent was concentrated under reduced pressure and co-evaporated with toluene to give 2-(4-chloro-2-methoxyphenyl)acetyl chloride 1a (6.5 g) as an oily residue that was used without further purification in the next step.

Synthesis of Intermediate 1b:

Diethylaluminum chloride 1M in hexane (37.1 mL, 37.14 mmol) was added dropwise at 0° C. to a solution of 6-fluoro-1H-indole [CAS 399-51-9] (3.34 g, 24.76 mmol) in $CH_2Cl_2$ (100 mL). After 30 min at 0° C., a solution of 2-(4-chloro-2-methoxyphenyl)acetyl chloride 1a (6.3 g, 28.76 mmol) in $CH_2Cl_2$ (100 mL) was added slowly at 0° C. The reaction was stirred at 0° C. for 3 h. Ice-water was added and the precipitate was filtered off, washed with water and a small amount of $CH_2Cl_2$. The solids were dried under vacuum at 70° C. overnight to give 2-(4-chloro-2-methoxyphenyl)-1-(6-fluoro-1H-indol-3-yl)ethanone 1b (4.9 g).

Synthesis of Intermediate 1c:

At 0° C., a solution of phenyltrimethylammonium tribromide [CAS 4207-56-1] (5.8 g, 15.4 mmol) in THF (65 mL) was added dropwise to a mixture of 2-(4-chloro-2-methoxyphenyl)-1-(6-fluoro-1H-indol-3-yl)ethanone 1b (4.9 g, 15.4 mmol) in THF (60 mL). The mixture was stirred at 0° C. for 1 h and at room temperature for 2.5 h. The precipitate was filtered off and washed with EtOAc. The filtrate was concentrated under reduced pressure. The residue was taken up with EtOAc and washed with water. A precipitate appeared in the organic layer and was filtered off and dried to provide a first batch of 2-bromo-2-(4-chloro-2-methoxyphenyl)-1-(6-fluoro-1H-indol-3-yl)ethanone 1c (4.6 g). The organic layer was separated, dried over $MgSO_4$, filtered and the solvent was evaporated under reduced pressure. The residue was crystallized from EtOAc, the precipitate was filtered off, washed with $Et_2O$ and dried under vacuum to provide a second fraction of 2-bromo-2-(4-chloro-2-methoxyphenyl)-1-(6-fluoro-1H-indol-3-yl)ethanone 1c (1.6 g).

Synthesis of Compound 1 and Chiral Separation into Enantiomers 1A and 1B:

A mixture of 2-bromo-2-(4-chloro-2-methoxyphenyl)-1-(6-fluoro-1H-indol-3-yl)-ethanone 1c (2.1 g, 5.3 mmol), 2-(3-amino-5-methoxyphenoxy)ethanol [CAS 725237-16-1] (924 mg, 5.05 mmol) and triethylamine (1.47 mL, 10.6 mmol) in $CH_3CN$ (16 mL) in a sealed tube was heated at 100° C. for 30 min using a microwave Biotage® Initiator EXP 60 with a power output ranging from 0 to 400 W (fixed hold time). The reaction was diluted with $CH_2Cl_2$ and the organic layer was washed with water, dried over $MgSO_4$, filtered and the solvent was concentrated under reduced pressure. The residue was purified by flash chromatography on silica gel (15-40 μm, 80 g) using a heptane/EtOAc gradient of 50/50 to 0/100. The pure fractions were collected and concentrated to give 1.1 g of Compound 1. This fraction was combined with another batch of 0.93 g of Compound 1 and subsequently purified via achiral SFC (Stationary phase: CYANO 6 μm 150×21.2 mm, Mobile phase: 75% $CO_2$, 25% MeOH) to provide 2-(4-chloro-2-methoxyphenyl)-1-(6-fluoro-1H-indol-3-yl)-2-((3-(2-hydroxyethoxy)-5-methoxyphenyl)amino)ethanone (Compound 1, 1.36 g) as a racemic mixture.

The enantiomers of Compound 1 (1.36 g) were separated via Chiral SFC (Stationary phase: Chiracel® OJ 20×250 mm, Mobile phase: 60% $CO_2$, 40% MeOH) yielding 611 mg of the first eluted enantiomer and 586 mg of the second eluted enantiomer. The first eluted enantiomer was taken up with $CH_3CN$/diisopropylether/heptane. The precipitate was filtered off and dried to give Enantiomer 1A (496 mg) as an amorphous powder. The second eluted enantiomer was taken up with $CH_3CN$/diisopropylether/heptane. The precipitate was filtered off and dried to give Enantiomer 1B (458 mg) as an amorphous powder.

Compound 1:

$^1$H NMR (500 MHz, DMSO-$d_6$) δ ppm 3.61 (s, 3 H) 3.64 (q, J=5.3 Hz, 2 H) 3.77-3.88 (m, 2 H) 3.96 (s, 3 H) 4.78 (t, J=5.5 Hz, 1 H) 5.71 (t, J=1.9 Hz, 1 H) 5.93 (d, J=1.9 Hz, 2 H) 6.15 (d, J=8.2 Hz, 1 H) 6.40 (d, J=8.2 Hz, 1 H) 6.96 (dd, J=8.2, 1.9 Hz, 1 H) 7.02-7.08 (m, 1 H) 7.09 (d, J=1.9 Hz, 1 H) 7.27 (dd, J=9.6, 2.4 Hz, 1 H) 7.35 (d, J=8.5 Hz, 1 H) 8.13 (dd, J=8.8, 5.7 Hz, 1 H) 8.43 (s, 1 H) 11.96-12.17 (m, 1 H)

LC/MS (method LC-C): $R_t$ 2.95 min, MH$^+$ 499

Enantiomer 1A:

$^1$H NMR (500 MHz, DMSO-$d_6$) δ ppm 3.57-3.68 (m, 5 H) 3.77-3.89 (m, 2 H) 3.96 (s, 3 H) 4.73-4.87 (m, 1 H) 5.71 (t, J=1.9 Hz, 1 H) 5.91-5.96 (m, 2 H) 6.15 (d, J=8.2 Hz, 1 H) 6.39 (d, J=8.2 Hz, 1 H) 6.96 (dd, J=8.2, 1.9 Hz, 1 H) 7.01-7.11 (m, 2 H) 7.27 (dd, J=9.6, 2.4 Hz, 1 H) 7.36 (d, J=8.2 Hz, 1 H) 8.13 (dd, J=9.6, 5.7 Hz, 1 H) 8.43 (s, 1 H) 11.45-12.31 (m, 1 H)

LC/MS (method LC-C): $R_t$ 2.95, MH$^+$ 499

$[\alpha]_D^{20}$: +112.1° (c 0.281, DMF)

Chiral SFC (method SFC-C): $R_t$ 3.17 min, MH$^+$ 499, chiral purity 100%.

Enantiomer 1B:

$^1$H NMR (500 MHz, DMSO-$d_6$) δ ppm 3.57-3.67 (m, 5 H) 3.74-3.90 (m, 2 H) 3.96 (s, 3 H) 4.78 (br. s., 1 H) 5.70-5.74 (m, 1 H) 5.93 (s, 2 H) 6.15 (d, J=8.2 Hz, 1 H) 6.40 (d, J=8.2 Hz, 1 H) 6.96 (dd, J=8.2, 1.9 Hz, 1 H) 7.02-7.08 (m, 1 H) 7.09 (d, J=1.9 Hz, 1 H) 7.27 (dd, J=9.6, 2.4 Hz, 1 H) 7.36 (d, J=8.2 Hz, 1 H) 8.13 (dd, J=9.6, 5.5 Hz, 1 H) 8.43 (s, 1 H) 11.63-12.47 (m, 1 H)

LC/MS (method LC-C): $R_t$ 2.95, MH$^+$ 499

$[\alpha]_D^{20}$: −113.9° (c 0.28, DMF)

Chiral SFC (method SFC-C): $R_t$ 4.12 min, MH$^+$ 499, chiral purity 100%.

Example 1.1

Chiral Stability of Enantiomer 1A at pH 7.4

The chiral stability of Enantiomer 1A (R=OMe) was evaluated by determination of the enantiomeric excess (ee %) after incubation for 24 h and 48 h in a buffered solution at pH 7.4 at 40° C. and 60° C. To assess the influence of the methoxy-substituent of Enantiomer 1A (R=OMe) on the stability against racemization, the chiral stability of Enantiomer 1'A (R=H) was tested under the same conditions.

To this end, 5 μM buffered (pH=7.4) solutions of 1A and 1'A were prepared by mixing 25 μL of a 100 μM solution of 1A or 1'A in DMSO with 475 μL aqueous buffer pH 7.4. Samples were taken 24 h and 48 h after incubation at 40° C. and 60° C. The analytical samples were analyzed by Chiral SFC (MS detection) and the chiral purity was expressed as the enantiomeric excess (ee %=% enantiomer A–% enantiomer B). Both Enantiomers 1A and 1'A had a chiral purity of 100% prior to their incubation.

1A (R = OMe)
1'A (R = H)

|          |             | ee %                    |     |
|----------|-------------|-------------------------|-----|
|          |             | Sampling timepoints (h) |     |
| Compound | Temperature | 24                      | 48  |
| 1A       | 40° C.      | 100                     | 100 |
|          | 60° C.      | 99                      | 96  |
| 1'A      | 40° C.      | 69                      | 41  |
|          | 60° C.      | 0                       | 0   |

Example 2

Synthesis of 2-(4-chloro-2-methoxyphenyl)-1-(6-fluoro-7-methyl-1H-indol-3-yl)-2-((3-(2-hydroxy-ethoxy)-5-methoxyphenyl)amino)ethanone (Compound 2) and Chiral Separation into Enantiomers 2A and 2B

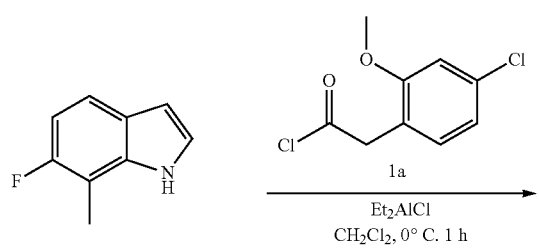

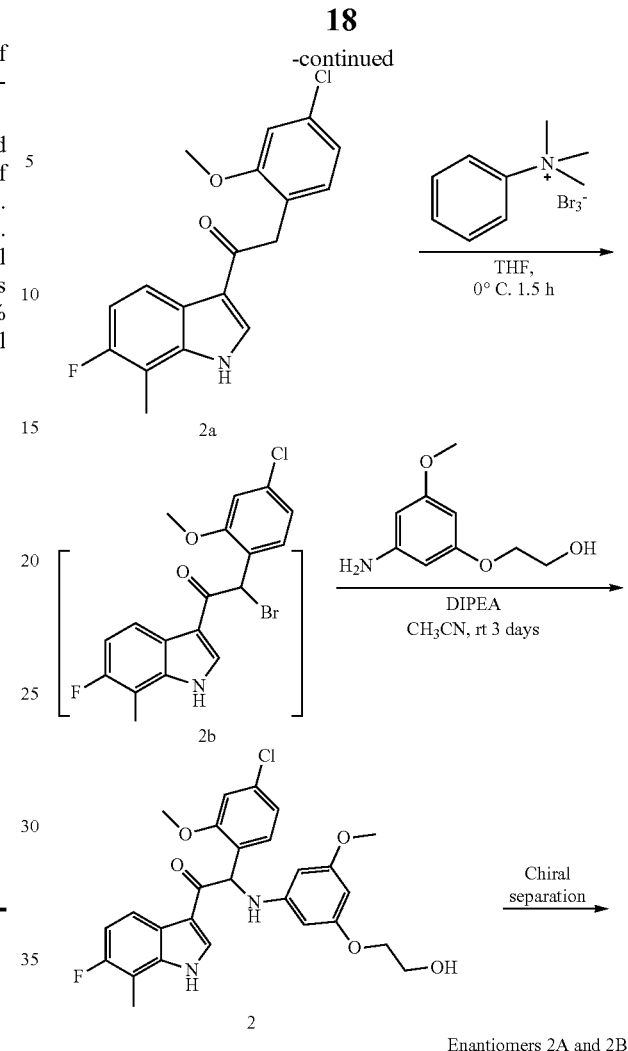

Enantiomers 2A and 2B

Synthesis of Intermediate 2a:

A solution of 6-fluoro-7-methyl-1H-indole [CAS 57817-10-4] (1.10 g, 7.37 mmol) in CH$_2$Cl$_2$ (40 mL) was cooled on an ice-bath under N$_2$-flow. Diethylaluminum chloride 1M in hexane (10 mL, 10 mmol) was added dropwise over 15 min. After additional stirring for 15 min at 0° C., a solution of 2-(4-chloro-2-methoxy-phenyl)acetyl chloride 1a (2.06 g, 9.42 mmol, synthesis: see example 1) in CH$_2$Cl$_2$ (35 mL) was added over 75 min at 0° C. The reaction was stirred at 0° C. for 1 h and subsequently quenched by slow addition of a solution of potassium sodium tartrate tetrahydrate (Rochelle salt) [CAS 6100-16-9] (4.24 g, 15 mmol) in water (10 mL), while keeping the internal temperature of the mixture below 10° C. The ice-bath was removed, 2-methyl-THF (160 mL) and Na$_2$SO$_4$ (60 g) were added and the resulting mixture was stirred at room temperature overnight. The mixture was filtered over dicalite® and the filter cake was washed with several portions of THF. The combined filtrates were evaporated under reduced pressure and the residue was triturated with a small amount of CH$_2$Cl$_2$. The solids were isolated by filtration and dried under vacuum to give 2-(4-chloro-2-methoxyphenyl)-1-(6-fluoro-7-methyl-1H-indol-3-yl)ethanone 2a (1.9 g) as a white powder.

Synthesis of Compound 2 and Chiral Separation into Enantiomers 2A and 2B:

A solution of 2-(4-chloro-2-methoxyphenyl)-1-(6-fluoro-7-methyl-1H-indol-3-yl)-ethanone 2a (1.9 g, 5.73 mmol) in dry THF (60 mL) was cooled on an ice-bath under N$_2$-flow. At 0° C., a solution of phenyltrimethylammonium tribromide [CAS 4207-56-1] (2.3 g, 5.91 mmol) in THF (50 mL) was added dropwise over a period of 1 h and the mixture was stirred at 0° C. for an additional 1.5 h. The reaction mixture was concentrated under reduced pressure and the residue, containing the crude brominated intermediate 2b, was dissolved in CH$_3$CN (100 mL). 2-(3-Amino-5-methoxyphenoxy)ethanol [CAS 725237-16-1] (2.11 g, 11.5 mmol) and diisopropylethylamine (2 mL, 11.6 mmol) were added and the reaction mixture was stirred at room temperature for 3 days. Water (350 mL) was added and the reaction products were extracted with 2-methyl-THF (3×100 mL). The combined organic layers were washed with 0.5 M HCl (200 mL) and water (3×300 mL), dried over MgSO$_4$ and evaporated under reduced pressure. The residue (2.48 g) was purified by column chromatography (Stationary phase: Silica 40 g, HP-Spher® 40 μm; Mobile phase: heptane/EtOAc gradient 100/0 to 0/100). The fractions containing reaction product were combined and evaporated under reduced pressure. The residue was triturated with a small amount of a mixture of EtOAc/heptane (1/1), the solids were filtered off and dried under vacuum to provide 2-(4-chloro-2-methoxyphenyl)-1-(6-fluoro-7-methyl-1H-indol-3-yl)-2-((3-(2-hydroxyethoxy)-5-methoxyphenyl)amino)ethanone (Compound 2, 1.38 g) as a racemic mixture. The enantiomers of Compound 2 (1.38 g) were separated via Preparative SFC (Stationary phase: Chiralpak® Diacel AS 20×250 mm, Mobile phase: CO$_2$, EtOH with 0.4% iPrNH$_2$). The first eluted enantiomer was dissolved in a mixture of MeOH (50 mL) and water (20 mL) and the mixture was evaporated under reduced pressure (200 mbar, water bath 40° C.) to a residual volume of 20 ml. The resulting suspension was diluted with 20 ml water and stirred at room temperature for 3 h. A white solid was filtered off, washed with water and dried under vacuum at room temperature to give Enantiomer 2A (631 mg) as an amorphous white powder. The second eluted enantiomer was dissolved in a mixture of MeOH (50 mL) and water (20 mL) and the mixture was evaporated under reduced pressure (200 mbar, water bath 40° C.) to a residual volume of 20 ml. The resulting suspension was diluted with 20 ml water and stirred at room temperature for 3 h. A white solid was filtered off, washed with water and dried under vacuum at room temperature to give Enantiomer 2B (625 mg) as an amorphous white powder.

Compound 2:

$^1$H NMR (400 MHz, DMSO-d$_6$) δ ppm 2.37 (br s, 3 H) 3.60 (s, 3 H) 3.63 (q, J=5.2 Hz, 2 H) 3.76-3.89 (m, 2 H) 3.96 (s, 3 H) 4.76 (t, J=5.5 Hz, 1 H) 5.71 (t, J=2.1 Hz, 1 H) 5.94 (d, J=2.2 Hz, 2 H) 6.16 (d, J=8.1 Hz, 1 H) 6.36 (d, J=8.1 Hz, 1 H) 6.95 (dd, J=8.4, 2.0 Hz, 1 H) 7.00 (dd, J=10.1, 8.8 Hz, 1 H) 7.08 (d, J=2.0 Hz, 1 H) 7.35 (d, J=8.1 Hz, 1 H) 7.95 (dd, J=8.7, 5.2 Hz, 1 H) 8.41 (s, 1 H) 12.17 (br s, 1 H)

LC/MS (method LC-A): R$_t$ 1.19 min, MH$^+$ 513

Enantiomer 2A:

$^1$H NMR (360 MHz, DMSO-d$_6$) δ ppm 2.38 (s, 3 H) 3.61 (s, 3 H) 3.62-3.67 (m, 2 H) 3.82 (ddt, J=15.4, 10.2, 5.1, 5.1 Hz, 2 H) 3.97 (s, 3 H) 4.81 (t, J=5.5 Hz, 1H) 5.71 (br t, J=1.8 Hz, 1 H) 5.95 (d, J=1.5 Hz, 2 H) 6.17 (br d, J=8.4 Hz, 1 H) 6.40 (br d, J=8.1 Hz, 1 H) 6.96 (dd, J=8.4, 1.8 Hz, 1 H) 7.02 (br dd, J=10.1, 9.0 Hz, 1 H) 7.10 (d, J=1.8 Hz, 1 H) 7.36 (d, J=8.1 Hz, 1 H) 7.96 (dd, J=8.6, 5.3 Hz, 1 H) 8.44 (s, 1 H) 12.22 (br s, 1 H)

LC/MS (method LC-A): R$_t$ 1.20, MH$^+$ 513

[α]$_D^{20}$ : +83.3° (c 0.36, DMF)

Chiral SFC (method SFC-F): R$_t$ 2.05 min, MH$^+$ 513, chiral purity 100%

Enantiomer 2B:

$^1$H NMR (360 MHz, DMSO-d$_6$) δ ppm 2.38 (s, 3 H) 3.61 (s, 3 H) 3.62-3.67 (m, 2 H) 3.83 (qt, J=10.2, 5.1 Hz, 2 H) 3.97 (s, 3 H) 4.80 (t, J=5.5 Hz, 1 H) 5.71 (br t, J=2.2 Hz, 1 H) 5.95 (d, J=1.8 Hz, 2 H) 6.17 (d, J=8.1 Hz, 1 H) 6.40 (d, J=8.1 Hz, 1 H) 6.96 (dd, J=8.4, 1.8 Hz, 1 H) 7.02 (dd, J=10.2, 8.8 Hz, 1 H) 7.10 (d, J=1.8 Hz, 1 H) 7.36 (d, J=8.1 Hz, 1 H) 7.96 (dd, J=8.6, 5.3 Hz, 1 H) 8.44 (s, 1 H) 12.21 (br s, 1 H)

LC/MS (method LC-A): R$_t$ 1.20, MH$^+$ 513

[α]$_D^{20}$: −81.9° (c 0.515, DMF)

Chiral SFC (method SFC-F): R$_t$ 3.28 min, MH$^+$ 513, chiral purity 100%

Example 3

Synthesis of 2-(4-chloro-2-methoxyphenyl)-1-(6-chloro-7-methyl-1H-indol-3-yl)-2-((3-(2-hydroxyethoxy)-5-methoxyphenyl)amino)ethanone (Compound 3) and Chiral Separation into Enantiomers 3A and 3B

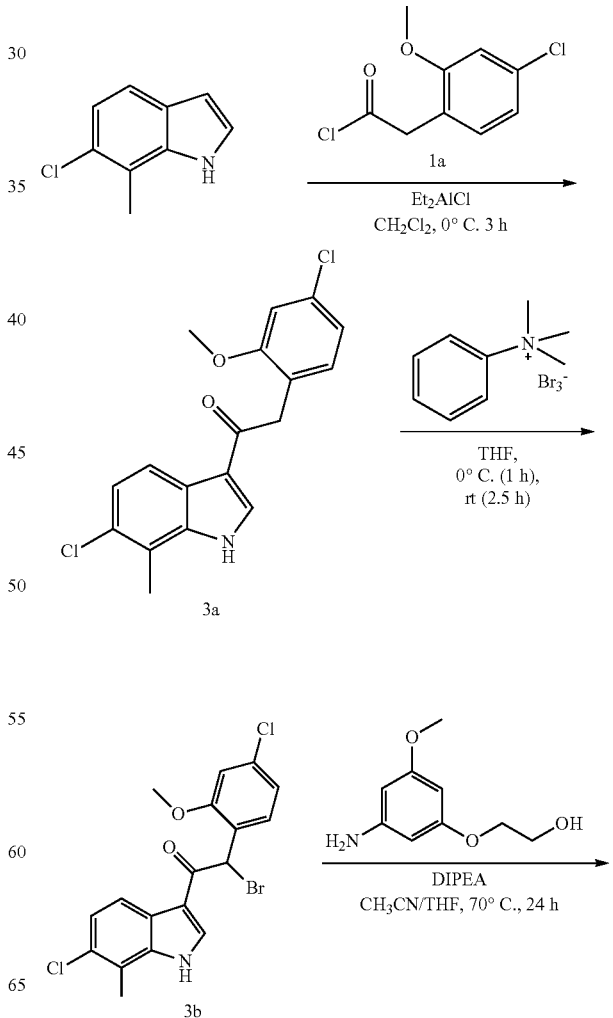

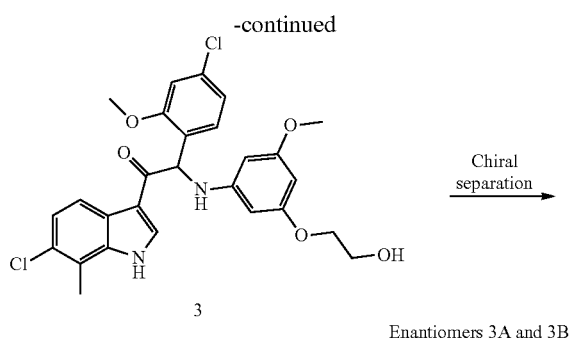

Enantiomers 3A and 3B

Synthesis of Intermediate 3a:

Diethylaluminum chloride 1M in hexane (18.1 mL, 18.1 mmol) was added dropwise at 0° C. to a solution of 6-chloro-7-methyl-1H-indole [CAS 57817-09-1] (2 g, 12.08 mmol) in $CH_2Cl_2$ (60 mL). After 30 min at 0° C., a solution of 2-(4-chloro-2-methoxyphenyl)acetyl chloride 1a (3.21 g, 14.66 mmol, synthesis: see example 1) in $CH_2Cl_2$ (60 mL) was added slowly at 0° C. The reaction was stirred at 0° C. for 3 h. Ice-water was added and the precipitate was filtered off and washed with water. The solid was dried under vacuum to give 2-(4-chloro-2-methoxyphenyl)-1-(6-chloro-7-methyl-1H-indol-3-yl)ethanone 3a (3.2 g).

Synthesis of Intermediate 3b:

At 0° C., a solution of phenyltrimethylammonium tribromide [CAS 4207-56-1] (3.63 g, 9.65 mmol) in THF (85 mL) was added dropwise to a solution of 2-(4-chloro-2-methoxyphenyl)-1-(6-chloro-7-methyl-1H-indol-3-yl)ethanone 3a (3.2 g, 9.2 mmol) in THF (85 mL). The mixture was stirred at 0° C. for 1 h and at room temperature for 2.5 h. The precipitate was filtered off and washed with EtOAc. The filtrate was concentrated under reduced pressure. The residue was taken up with a minimum of $CH_3CN$/diisopropylether. The precipitate was filtered off and dried under vacuum to give 2-bromo-2-(4-chloro-2-methoxyphenyl)-1-(6-chloro-7-methyl-1H-indol-3-yl)ethanone 3b (4.1 g).

Synthesis of Compound 3 and Chiral Separation into Enantiomers 3A and 3B:

A mixture of 2-bromo-2-(4-chloro-2-methoxyphenyl)-1-(6-chloro-7-methyl-1H-indol-3-yl)ethanone 3b (3.1 g, 7.26 mmol), 2-(3-amino-5-methoxyphenoxy)ethanol [CAS 725237-16-1] (1.33 g, 7.26 mmol) and diisopropylethylamine (1.9 mL, 10.9 mmol) in $CH_3CN$/THF (1/1) (120 mL) was stirred at 70° C. for 24 h. The mixture was concentrated under reduced pressure. The residue was diluted with $CH_2Cl_2$ and washed with 1N HCl. The organic layer was separated, dried over $MgSO_4$, filtered and the solvent was evaporated under reduced pressure. The residue was purified by column chromatography on silica gel (15-40 μm, 80 g in $CH_2Cl_2$/MeOH (99.5/0.5)). The pure fractions were collected and evaporated under reduced pressure (2.3 g). A small amount was crystallized from $Et_2O$/$CH_3CN$ to provide an analytical sample of 2-(4-chloro-2-methoxyphenyl)-1-(6-chloro-7-methyl-1H-indol-3-yl)-2-((3-(2-hydroxyethoxy)-5-methoxyphenyl)amino)ethanone (Compound 3) as a racemate.

The Enantiomers of Compound 3 (2.2 g) were separated via Preparative Chiral SFC (Stationary phase: (S,S) Whelk-O 1 5 μm 250×21.1 mm, Mobile phase: 45% $CO_2$, 55% EtOH (+2% $CH_2Cl_2$)) to give 1.11 g of the first eluted enantiomer and 1.07 g of the second eluted enantiomer. The first eluted enantiomer was solidified from $CH_3CN$/$Et_2O$/heptane to afford Enantiomer 3A (461 mg) as an amorphous white powder. The second eluted enantiomer was solidified from $CH_3CN$/$Et_2O$/heptane to afford Enantiomer 3B (872 mg) as an amorphous white powder.

Compound 3:

$^1$H NMR (500 MHz, DMSO-$d_6$) δ ppm 12.26 (d, J=2.8 Hz, 1 H) 8.46 (d, J=3.2 Hz, 1 H) 7.97 (d, J=8.5 Hz, 1 H) 7.35 (d, J=8.2 Hz, 1 H) 7.22 (d, J=8.5 Hz, 1 H) 7.09 (d, J=1.9 Hz, 1 H) 6.96 (dd, J=8.2, 1.9 Hz, 1 H) 6.40 (d, J=8.2 Hz, 1 H) 6.18 (d, J=8.2 Hz, 1 H) 5.95 (d, J=2.2 Hz, 2 H) 5.71 (t, J=2.2 Hz, 1 H) 4.79 (t, J=5.5 Hz, 1 H) 3.96 (s, 3 H) 3.77-3.89 (m, 2 H) 3.58-3.67 (m, 5 H)

LC/MS (method LC-C): $R_t$ 3.28 min, MH$^+$ 529

Melting point: 220° C.

Enantiomer 3A:

$^1$H NMR (500 MHz, DMSO-$d_6$) δ ppm 12.26 (br. s., 1 H) 8.46 (s, 1 H) 7.97 (d, J=8.2 Hz, 1 H) 7.36 (d, J=8.2 Hz, 1 H) 7.21 (d, J=8.5 Hz, 1 H) 7.10 (d, J=1.9 Hz, 1 H) 6.96 (dd, J=8.2, 1.9 Hz, 1 H) 6.40 (d, J=7.9 Hz, 1 H) 6.18 (d, J=8.2 Hz, 1 H) 5.95 (d, J=2.2 Hz, 2 H) 5.71 (t, J=2.0 Hz, 1 H) 4.79 (t, J=5.5 Hz, 1 H) 3.97 (s, 3 H) 3.77-3.89 (m, 2 H) 3.59-3.67 (m, 5 H)

LC/MS (method LC-C): $R_t$ 3.27 min, MH$^+$ 529

$[α]_D^{20}$: +88.8° (c 0.2691, DMF)

Chiral SFC (method SFC-E): $R_t$ 3.40 min, MH$^+$ 529, chiral purity 100%.

Enantiomer 3B:

$^1$H NMR (500 MHz, DMSO-$d_6$) δ ppm 12.26 (br. s., 1 H) 8.45 (s, 1 H) 7.97 (d, J=8.5 Hz, 1 H) 7.36 (d, J=8.5 Hz, 1 H) 7.21 (d, J=8.5 Hz, 1 H) 7.09 (d, J=1.9 Hz, 1 H) 6.96 (dd, J=8.2, 1.9 Hz, 1 H) 6.40 (d, J=8.2 Hz, 1 H) 6.18 (d, J=8.2 Hz, 1 H) 5.95 (d, J=2.2 Hz, 2 H) 5.71 (t, J=2.0 Hz, 1 H) 4.79 (t, J=5.5 Hz, 1 H) 3.97 (s, 3H) 3.76-3.90 (m, 2 H) 3.60-3.66 (m, 5 H)

LC/MS (method LC-C): $R_t$ 3.27 min, MH$^+$ 529

$[α]_D^{20}$: −87.4° (c 0.2564, DMF)

Chiral SFC (method SFC-E): $R_t$ 4.19 min, MH$^+$ 529, chiral purity 100%.

Example 4

Synthesis of 1-(6-chloro-1H-indol-3-yl)-2-(4-chloro-2-methoxyphenyl)-2-((3-(2-hydroxyethoxy)-5-methoxyphenyl)amino)ethanone (Compound 4) and Chiral Separation into Enantiomers 4A and 4B

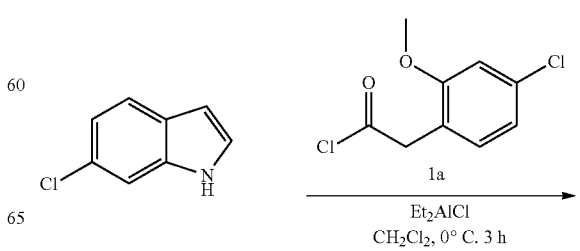

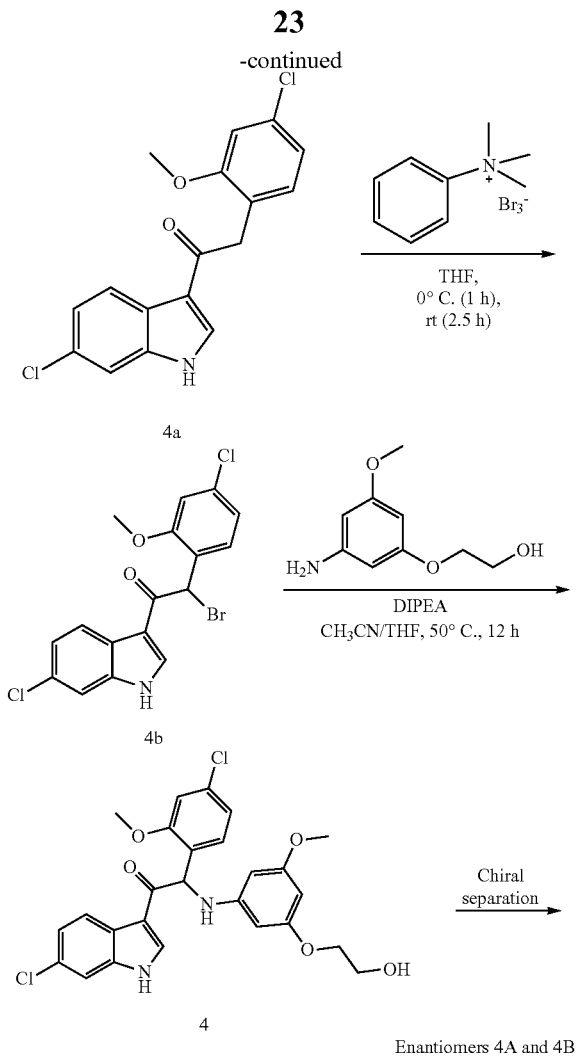

Synthesis of Intermediate 4a:

Diethylaluminum chloride 1M in hexane (19.8 mL, 19.8 mmol) was added dropwise at 0° C. to a solution of 6-chloro-1H-indole [CAS 17422-33-2] (2 g, 13.2 mmol) in CH$_2$Cl$_2$ (45 mL). After 30 min at 0° C., a solution of 2-(4-chloro-2-methoxyphenyl)acetyl chloride 1a (3.36 g, 15.3 mmol, synthesis: see example 1) in CH$_2$Cl$_2$ (45 mL) was added slowly at 0° C. The reaction was stirred at 0° C. for 3 h. Ice-water was added and the precipitate was filtered off, washed with water and the minimum of CH$_2$Cl$_2$. The solid was dried under vacuum to give 1-(6-chloro-1H-indol-3-yl)-2-(4-chloro-2-methoxyphenyl)ethanone 4a (2.68 g).

Synthesis of Intermediate 4b:

At 0° C., a solution of phenyltrimethylammonium tribromide [CAS 4207-56-1] (3.165 g, 8.4 mmol) in THF (50 mL) was added dropwise to a solution of 1-(6-chloro-1H-indol-3-yl)-2-(4-chloro-2-methoxyphenyl)ethanone 4a (2.68 g, 8 mmol) in THF (50 mL). The mixture was stirred at 0° C. for 1 h and at room temperature for 2.5 h. The precipitate was filtered off and washed with EtOAc. The filtrate was concentrated under reduced pressure. The residue was dissolved in EtOAc and washed with water. A precipitate appeared and the solids were filtered off and dried under vacuum to give 2-bromo-1-(6-chloro-1H-indol-3-yl)-2-(4-chloro-2-methoxyphenyl)ethanone 4b (2.75 g).

Synthesis of Compound 4 and Chiral Separation into Enantiomers 4A and 4B:

A mixture of 2-bromo-1-(6-chloro-1H-indol-3-yl)-2-(4-chloro-2-methoxyphenyl)-ethanone 4b (2.3 g, 5.6 mmol), 2-(3-amino-5-methoxyphenoxy)ethanol [CAS 725237-16-1] (1.53 g, 8.4 mmol) and diisopropylethylamine (2.4 mL, 13.9 mmol) in CH$_3$CN/THF (1/1) (140 mL) was stirred at 50° C. for 12 h. The mixture was concentrated under reduced pressure. The residue was diluted with EtOAc, washed with 1N HCl, and then with water. The organic layer was dried over MgSO$_4$, filtered and the solvent was evaporated under reduced pressure. The crude compound was purified by column chromatography on silica gel (15-40 µm, 80 g in CH$_2$Cl$_2$/MeOH (99.5/0.5)). The pure fractions were collected and evaporated under reduced pressure. A small amount was crystallized from Et$_2$O/CH$_3$CN to give an analytical sample of 1-(6-chloro-1H-indol-3-yl)-2-(4-chloro-2-methoxyphenyl)-2-((3-(2-hydroxyethoxy)-5-methoxyphenyl)amino)ethanone (Compound 4) as a racemic mixture. The remaining amount of Compound 4 (2.1 g) was further purified via preparative LC (Stationary phase: irregular bare silica 150 g, mobile phase: toluene/iPrOH 95/5).

The Enantiomers of Compound 4 (1.9 g) were separated via Preparative Chiral SFC (Stationary phase: Chiralpak® IC 5 µm 250×30 mm, Mobile phase: 60% CO$_2$, 40% MeOH) to give 870 mg of the first eluted enantiomer and 870 mg of the second eluted enantiomer. The two enantiomers were purified again by flash chromatography on silica gel (15-40 µm, 24 g in CH$_2$Cl$_2$/MeOH (99.5/0.5)). The first eluted enantiomer (800 mg) was solidified from CH$_3$CN/Et$_2$O to afford Enantiomer 4A (693 mg) as an amorphous white powder. The second eluted enantiomer was solidified from CH$_3$CN/Et$_2$O to afford Enantiomer 4B (619 mg) as an amorphous white powder.

Compound 4:

$^1$H NMR (500 MHz, DMSO-d$_6$) δ ppm 3.60 (s, 3 H) 3.64 (t, J=5.0 Hz, 2 H) 3.75-3.88 (m, 2 H) 3.95 (s, 3 H) 4.38-5.09 (m, 1 H) 5.71 (t, J=1.9 Hz, 1 H) 5.93 (d, J=2.2 Hz, 2 H) 6.13-6.18 (m, 1 H) 6.35-6.46 (m, 1 H) 6.97 (dd, J=8.4, 1.9 Hz, 1 H) 7.09 (d, J=2.2 Hz, 1 H) 7.21 (dd, J=8.5, 1.9 Hz, 1 H) 7.35 (d, J=8.4 Hz, 1 H) 7.53 (d, J=1.9 Hz, 1 H) 8.13 (d, J=8.5 Hz, 1 H) 8.46 (d, J=2.8 Hz, 1 H) 12.13 (d, J=2.8 Hz, 1 H)

LC/MS (method LC-C): R$_t$ 3.11 min, MH$^+$ 515

Melting point: 154° C.

Enantiomer 4A:

$^1$H NMR (500 MHz, DMSO-d$_6$) δ ppm 3.60 (s, 3 H) 3.64 (q, J=5.0 Hz, 2 H) 3.74-3.88 (m, 2 H) 3.95 (s, 3 H) 4.79 (t, J=5.0 Hz, 1 H) 5.71 (d, J=2.0 Hz, 1 H) 5.93 (d, J=2.0 Hz, 2 H) 6.15 (d, J=7.9 Hz, 1 H) 6.41 (d, J=8.2 Hz, 1 H) 6.97 (dd, J=8.2, 1.9 Hz, 1 H) 7.09 (d, J=1.9 Hz, 1 H) 7.21 (dd, J=8.5, 1.9 Hz, 1 H) 7.35 (d, J=8.2 Hz, 1 H) 7.53 (d, J=1.9 Hz, 1 H) 8.13 (d, J=8.5 Hz, 1 H) 8.46 (s, 1 H) 12.12 (br. s., 1 H)

LC/MS (method LC-C): R$_t$ 3.13 min, MH$^+$ 515

[α]$_D^{20}$: +111.6° (c 0.284, DMF)

Chiral SFC (method SFC-A): R$_t$ 3.68 min, MH$^+$ 515, chiral purity 100%.

Enantiomer 4B:

$^1$H NMR (500 MHz, DMSO-d$_6$) δ ppm 3.61 (s, 3 H) 3.62-3.68 (m, 2 H) 3.76-3.89 (m, 2 H) 3.95 (s, 3 H) 4.74-4.83 (m, 1 H) 5.72 (t, J=2.0 Hz, 1 H) 5.93 (d, J=2.0 Hz, 2 H) 6.15 (d, J=7.9 Hz, 1 H) 6.42 (d, J=8.2 Hz, 1 H) 6.97 (dd, J=8.2, 1.9 Hz, 1 H) 7.09 (d, J=1.9 Hz, 1 H) 7.21 (dd, J=8.5, 1.9 Hz, 1 H) 7.35 (d, J=8.2 Hz, 1 H) 7.53 (d, J=1.9 Hz, 1 H) 8.13 (d, J=8.5 Hz, 1 H) 8.46 (s, 1 H) 12.13 (br. s., 1 H)

LC/MS (method LC-C): $R_t$ 3.14 min, MH+ 515

$[\alpha]_D^{20}$: −113.9° (c 0.288, DMF)

Chiral SFC (method SFC-A): $R_t$ 5.04 min, MH+ 515, chiral purity 100%.

Example 5

Synthesis 2-(4-chloro-2-methoxyphenyl)-2-((3-(2-hydroxyethoxy)-5-methoxyphenyl)amino)-1-(6-methoxy-1H-indol-3-yl)ethanone (Compound 5) and Chiral Separation into Enantiomers 5A and 5B

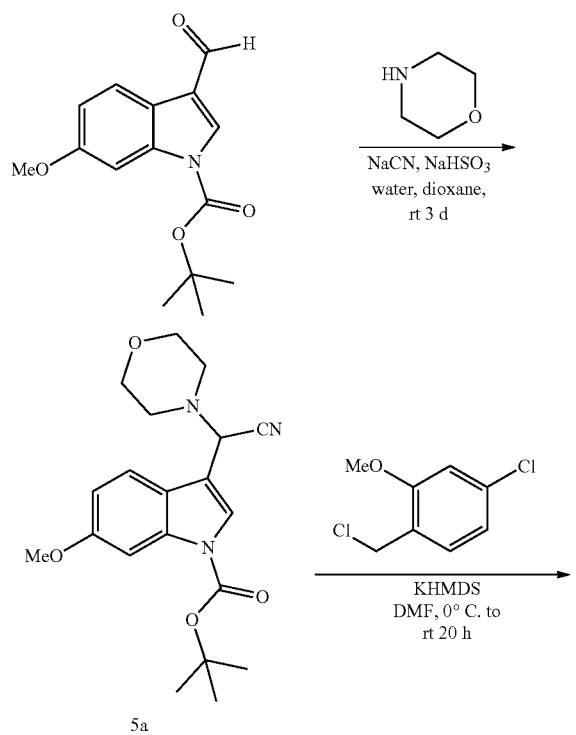

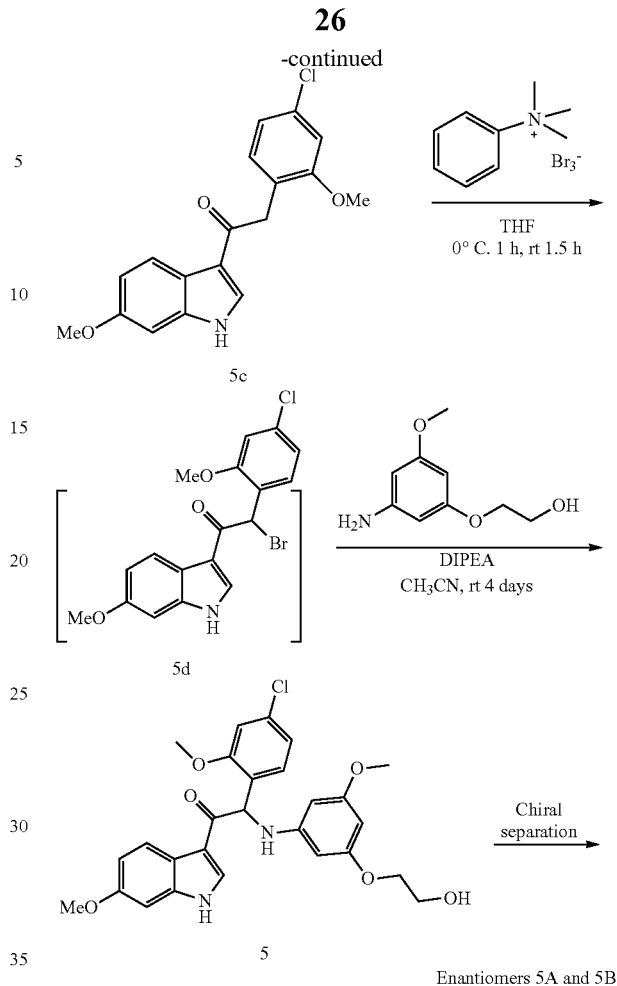

Enantiomers 5A and 5B

Synthesis of Intermediate 5a:

A solution of NaHSO₃ (5.7 g, 54.5 mmol) in water (45 mL) was added to a stirring solution of tert-butyl 3-formyl-6-methoxy-1H-indole-1-carboxylate [CAS 847448-73-1] (10 g, 36.3 mmol) in dioxane (45 mL). After 15 min, morpholine (4.8 mL, 54.5 mmol) was added and 35 min later, sodium cyanide (NaCN) (1.96 g, 40 mmol) was added. The resulting suspension was stirred at room temperature for 3 days, until completion of the reaction. The product was filtered off and washed with a 1/1 mixture of dioxane/water (3×35 mL) and subsequently with water (3×45 mL) and dried under vacuum at 60° C. The solids were stirred up in Et₂O (125 mL), filtered off, washed with Et₂O (3×) and dried under vacuum at 50° C. to provide tert-butyl 3-(cyano (morpholino)methyl)-6-methoxy-1H-indole-1-carboxylate 5a (12.3 g).

Synthesis of Intermediate 5b:

A mixture of tert-butyl 3-(cyano(morpholino)methyl)-6-methoxy-1H-indole-1-carboxylate 5a (6.0 g, 16.2 mmol) in dry DMF (80 mL) was stirred under N₂-atmosphere while cooling on an ice-bath. A solution of KHMDS 0.5 M in toluene (35.5 mL, 17.8 mmol) was added dropwise over 10 min. After stirring for an additional 10 min, 4-chloro-1-(chloromethyl)-2-methoxybenzene [CAS 101079-84-9] (3.09 g, 16.2 mmol) was added and the resulting mixture was stirred at room temperature for 20 h. The reaction mixture was poured into cold water (400 mL) and the product was extracted with Et₂O (2×). The combined organic layers were washed with brine, dried over MgSO₄, filtered, evaporated under reduced pressure and co-evaporated with xylene. The residue was purified by flash chromatography (Stationary phase: Biotage® Grace Reveleris Silica 120 g, Mobile phase: heptane/EtOAc gradient 100/0 to 20/80). The desired fractions were combined, evaporated under reduced pressure and co-evaporated with dioxane to give tert-butyl 3-(2-(4-chloro-2-methoxyphenyl)-1-cyano-1-morpholinoethyl)-6-methoxy-1H-indole-1-carboxylate 5b (7.75 g).

Synthesis of Intermediate 5c:

To a stirred suspension of tert-butyl 3-(2-(4-chloro-2-methoxyphenyl)-1-cyano-1-morpholinoethyl)-6-methoxy-1H-indole-1-carboxylate 5b (7.75 g, 14.7 mmol) in dioxane (40 mL) and water (20 mL) was added a solution of HCl 6M in isopropanol (36.8 mL, 220 mmol). The resulting mixture was stirred at 60° C. for 4 h and subsequently at 80° C. for 1 hour. After cooling to room temperature, the mixture was left standing for 20 h to allow crystallization of the reaction product. The product was filtered off, washed with a 1/1/1 mixture of iPrOH/H$_2$O/dioxane (2×15 mL) and dried under vacuum at 50° C. to give 2-(4-chloro-2-methoxyphenyl)-1-(6-methoxy-1H-indol-3-yl)ethanone 5c (3.67 g).

Synthesis of Compound 5 and Chiral Separation into Enantiomers 5A and 5B:

A stirred mixture of 2-(4-chloro-2-methoxyphenyl)-1-(6-methoxy-1H-indol-3-yl)-ethanone 5c (2.35 g, 7.13 mmol) in THF (100 mL) was cooled on an ice-bath under N$_2$-atm. Phenyltrimethylammonium tribromide [CAS 4207-56-1] (2.81 g, 7.48 mmol) was added and the reaction mixture was stirred at 0° C. for 1 h and subsequently at room temperature for 1.5 h. 2-(3-Amino-5-methoxyphenoxy)ethanol [CAS 725237-16-1] (2.61 g, 14.3 mmol), diisopropylethylamine (2.46 mL, 14.3 mmol) and CH$_3$CN (100 mL) were added and the reaction mixture was stirred at room temperature for 18 h and at 55° C. for 2 h. The reaction mixture was concentrated under reduced pressure to 50% of the original volume. 2-(3-Amino-5-methoxyphenoxy)ethanol [CAS 725237-16-1] (1 g) and diisopropylethylamine (1.5 mL) were added and the reaction mixture was stirred at room temperature for 65 h. The reaction mixture was poured out into water (400 mL) and the product was extracted with 2-MeTHF (2×). The combined organic layers were washed with brine, dried over MgSO$_4$, filtered and evaporated under reduced pressure. The residue (7 g) was purified by flash chromatography (stationary phase: Biotage® Grace Reveleris Silica 120 g, Mobile phase: heptane/EtOAc/EtOH gradient 100/0/0 to 50/37/13). The desired fractions were combined and evaporated under reduced pressure. The residue (5.8 g) was further purified by Preparative HPLC (Stationary phase: Uptisphere® C18 ODB—10 µm, 200 g, 5 cm, Mobile phase: 0.25% NH$_4$HCO$_3$ solution in water, CH$_3$CN). The product fractions were combined and evaporated under reduced pressure. The residue was dissolved in MeOH (20 mL) and left standing to crystallize for 4 h. the solids were filtered off, washed with MeOH (3×5 mL) and dried under vacuum at 50° C. to provide 2-(4-chloro-2-methoxyphenyl)-2-((3-(2-hydroxyethoxy)-5-methoxyphenyl)amino)-1-(6-methoxy-1H-indol-3-yl)ethanone (Compound 5, 2.06 g) as a racemic mixture.

Chiral separation of Compound 5 (2 g) was performed via Normal Phase Chiral separation (Stationary phase: AD-H, Mobile phase: 50% methanol, 50% ethanol). The product fractions were combined and evaporated under reduced pressure. The first eluted enantiomer was crystallized from a stirring solution of MeOH (13 mL) by addition of water (3 mL). After overnight stirring, the solids were filtered off, washed with a 3/1 mixture of MeOH/H$_2$O (4×3 mL) and dried under vacuum at 50° C. to provide Enantiomer 5A (476 mg). The second eluted enantiomer was crystallized from a stirring solution of MeOH (13 mL) by addition of water (3 mL). After overnight stirring, the solids were filtered off, washed with a 3/1 mixture of MeOH/H$_2$O (4×3 mL) and dried under vacuum at 50° C. to provide Enantiomer 5B (362 mg).

Compound 5:

$^1$H NMR (400 MHz, DMSO-d$_6$) δ ppm 3.61 (s, 3 H) 3.65 (q, J=5.3 Hz, 2 H) 3.77 (s, 3 H) 3.78-3.90 (m, 2 H) 3.97 (s, 3 H) 4.77 (t, J=5.6 Hz, 1 H) 5.71 (t, J=2.1 Hz, 1 H) 5.93 (d, J=2.2 Hz, 2 H) 6.13 (d, J=8.1 Hz, 1 H) 6.36 (d, J=7.9 Hz, 1 H) 6.83 (dd, J=8.7, 2.3 Hz, 1 H) 6.92-7.00 (m, 2 H) 7.09 (d, J=2.0 Hz, 1 H) 7.36 (d, J=8.4 Hz, 1 H) 8.01 (d, J=8.6 Hz, 1 H) 8.29 (d, J=2.9 Hz, 1 H) 11.81 (br d, J=2.2 Hz, 1 H)

LC/MS (method LC-B): R$_t$ 1.93, MH$^+$ 511

Enantiomer 5A:

$^1$H NMR (400 MHz, DMSO-d$_6$) δ ppm 3.61 (s, 3 H) 3.64 (q, J=5.4 Hz, 2 H) 3.77 (s, 3 H) 3.78-3.90 (m, 2 H) 3.97 (s, 3 H) 4.77 (t, J=5.5 Hz, 1 H) 5.71 (t, J=2.0 Hz, 1 H) 5.93 (d, J=2.0 Hz, 2 H) 6.13 (d, J=8.1 Hz, 1 H) 6.36 (d, J=7.9 Hz, 1 H) 6.83 (dd, J=8.7, 2.3 Hz, 1 H) 6.92-6.99 (m, 2 H) 7.09 (d, J=2.0 Hz, 1 H) 7.36 (d, J=8.4 Hz, 1 H) 8.01 (d, J=8.8 Hz, 1 H) 8.29 (d, J=3.1 Hz, 1 H) 11.81 (br d, J=2.4 Hz, 1 H)

LC/MS (method LC-A): R$_t$ 1.08, MH$^+$ 511

$[\alpha]_D^{20}$: +109.3° (c 0.61, DMF)

Chiral SFC (method SFC-G): R$_t$ 1.78 min, MH$^+$ 511, chiral purity 100%

Enantiomer 5B:

$^1$H NMR (400 MHz, DMSO-d$_6$) δ ppm 3.61 (s, 3 H) 3.64 (q, J=5.2 Hz, 2 H) 3.77 (s, 3 H) 3.78-3.89 (m, 2 H) 3.97 (s, 3 H) 4.77 (t, J=5.6 Hz, 1 H) 5.71 (t, J=2.1 Hz, 1 H) 5.93 (d, J=2.0 Hz, 2 H) 6.12 (d, J=7.9 Hz, 1 H) 6.35 (d, J=7.9 Hz, 1 H) 6.82 (dd, J=8.7, 2.3 Hz, 1 H) 6.91-7.01 (m, 2 H) 7.09 (d, J=2.0 Hz, 1 H) 7.36 (d, J=8.1 Hz, 1 H) 8.01 (d, J=8.6 Hz, 1 H)

LC/MS (method LC-A): R$_t$ 1.08, MH$^+$ 511

$[\alpha]_D^{20}$: −108.9° (c 0.52, DMF)

Chiral SFC (method SFC-G): R$_t$ 2.19 min, MH$^+$ 511, chiral purity 100%

Example 6

Synthesis of 2-(4-chloro-2-methoxyphenyl)-2-((3-(2-hydroxyethoxy)-5-methoxyphenyl)amino)-1-(6-methoxy-5-methyl-1H-indol-3-yl)ethanone (Compound 6) and Chiral Separation into Enantiomers 6A and 6B

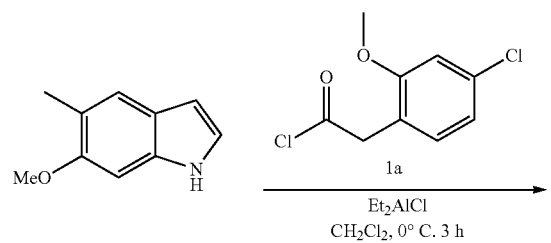

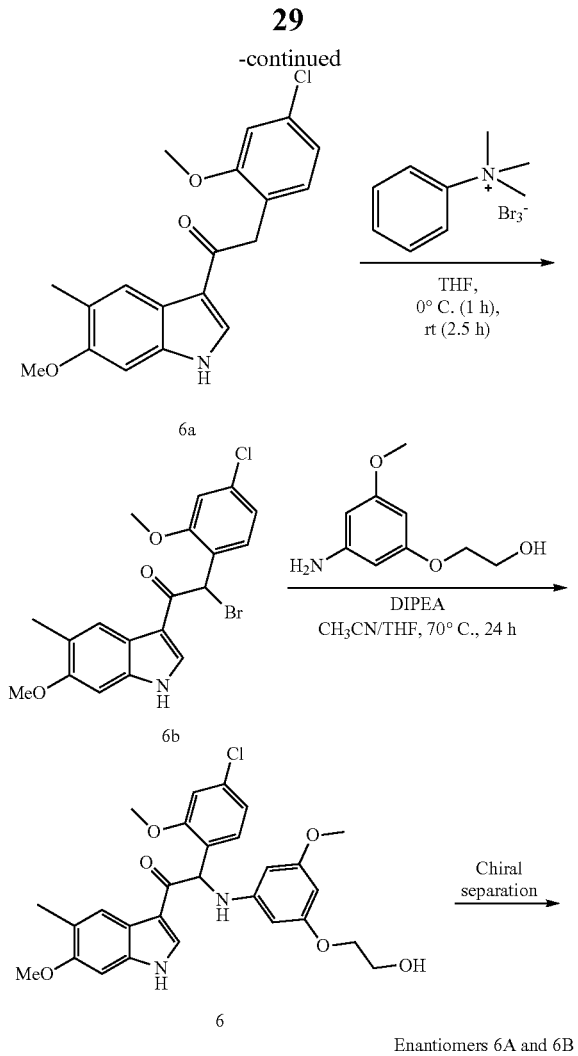

Synthesis of Intermediate 6a:

Diethylaluminum chloride 1M in hexane (13.5 mL, 13.5 mmol) was added dropwise at 0° C. to a solution of 6-methoxy-5-methyl-1H-indole [CAS 1071973-95-9] (1.45 g, 9 mmol) in $CH_2Cl_2$ (45 mL). After 30 min at 0° C., a solution of 2-(4-chloro-2-methoxyphenyl)acetyl chloride 1a (2.4 g, 10.9 mmol, synthesis: see example 1) in $CH_2Cl_2$ (45 mL) was added slowly at 0° C. The reaction was stirred at 0° C. for 3 h. Ice-water was added and the precipitate was filtered off and washed with water. The solid was dried under vacuum to give 2-(4-chloro-2-methoxyphenyl)-1-(6-methoxy-5-methyl-1H-indol-3-yl)ethanone 6a (2.1 g).

Synthesis of Intermediate 6b:

At 0° C., a solution of phenyltrimethylammonium tribromide [CAS 4207-56-1] (2.4 g, 6.4 mmol) in THF (65 mL) was added dropwise to a mixture of 2-(4-chloro-2-methoxyphenyl)-1-(6-methoxy-5-methyl-1H-indol-3-yl)ethanone 6a (2.1 g, 6.1 mmol) in THF (60 mL). The mixture was stirred at 0° C. for 1 h and at room temperature for 2.5 h. The precipitate was filtered off and washed with EtOAc. The filtrate was concentrated under reduced pressure. The residue was taken up with the minimum of diisopropylether. The precipitate was filtered off and dried under vacuum to give 2-bromo-2-(4-chloro-2-methoxyphenyl)-1-(6-methoxy-5-methyl-1H-indol-3-yl)ethanone 6b (2.36 g).

Synthesis of Compound 6 and Chiral Separation into Enantiomers 6A and 6B:

A mixture of 2-bromo-2-(4-chloro-2-methoxyphenyl)-1-(6-methoxy-5-methyl-1H-indol-3-yl)ethanone 6b (1.35 g, 3.2 mmol), 2-(3-amino-5-methoxyphenoxy)ethanol [CAS 725237-16-1] (0.585 g, 3.2 mmol) and diisopropylethylamine (0.83 mL, 4.8 mmol) in $CH_3CN/THF$ (1/1) (80 mL) was stirred at 70° C. for 24 h. The mixture was concentrated under reduced pressure. The residue was diluted with $CH_2Cl_2$, washed with 1N HCl and water. The organic layer was separated, dried over $MgSO_4$, filtered and the solvent was evaporated under reduced pressure. The crude compound was purified by column chromatography on silica gel (15-40 μm, 80 g in $CH_2Cl_2/MeOH$ (99.5/0.5)). A small amount was crystallized from $Et_2O/CH_3CN$ to give an analytical sample of 2-(4-chloro-2-methoxyphenyl)-2-((3-(2-hydroxyethoxy)-5-methoxyphenyl)amino)-1-(6-methoxy-5-methyl-1H-indol-3-yl)ethanone (Compound 3) as a racemic mixture. The remaining amount of crude Compound 3 was mixed with another batch (total amount 1.19 g) and was further purified twice via preparative LC (Stationary phase: irregular bare silica 150 g, Mobile phase: $CH_2Cl_2/MeOH$ (98/2), and then toluene/iPrOH (95/5).

The Enantiomers of Compound 3 (950 mg) were separated via Preparative Chiral SFC (Stationary phase: Chiralpak® IC 5 μm 250×30 mm, Mobile phase: 50% $CO_2$, 50% MeOH) to give 485 mg of the first eluted enantiomer and 480 mg of the second eluted enantiomer. The first eluted enantiomer was solidified from $CH_3CN/Et_2O$ to afford Enantiomer 6A (406 mg) as an amorphous white powder. The second eluted enantiomer was solidified from $CH_3CN/Et_2O$ to afford Enantiomer 6B (436 mg) as an amorphous white powder.

Compound 6:

$^1$H NMR (400 MHz, DMSO-$d_6$) δ ppm 2.21 (s, 3 H) 3.61 (s, 3 H) 3.62-3.68 (m, 2 H) 3.74-3.90 (m, 5 H) 3.97 (s, 3 H) 4.76 (t, J=4.8 Hz, 1 H) 5.68-5.74 (m, 1H) 5.93 (d, J=1.5 Hz, 2 H) 6.11 (d, J=7.6 Hz, 1 H) 6.31 (d, J=7.6 Hz, 1 H) 6.92 (s, 1 H) 6.95 (dd, J=8.3, 1.8 Hz, 1 H) 7.09 (d, J=1.8 Hz, 1 H) 7.35 (d, J=8.3 Hz, 1 H) 7.89 (s, 1 H) 8.22 (s, 1 H) 11.73 (br. s., 1 H)

LC/MS (method LC-C): $R_t$ 3.02 min, MH$^+$ 525

Enantiomer 6A:

$^1$H NMR (500 MHz, DMSO-$d_6$) δ ppm 2.20 (s, 3 H) 3.60 (s, 3 H) 3.64 (q, J=5.3 Hz, 2 H) 3.75-3.88 (m, 5 H) 3.97 (s, 3 H) 4.78 (t, J=5.3 Hz, 1 H) 5.70 (t, J=2.0 Hz, 1 H) 5.92 (d, J=2.0 Hz, 2 H) 6.11 (d, J=7.9 Hz, 1 H) 6.33 (d, J=7.9 Hz, 1 H) 6.92 (s, 1 H) 6.95 (dd, J=8.2, 1.9 Hz, 1 H) 7.09 (d, J=1.9 Hz, 1 H) 7.35 (d, J=8.2 Hz, 1 H) 7.88 (s, 1 H) 8.23 (s, 1 H) 11.75 (br. s., 1 H)

LC/MS (method LC-C): $R_t$ 3.04 min, MH$^+$ 525

$[\alpha]_D^{20}$: +116.8° (c 0.4536, DMF)

Chiral SFC (method SFC-B): $R_t$ 2.40 min, MH$^+$ 525, chiral purity 100%.

Enantiomer 6B:

$^1$H NMR (500 MHz, DMSO-$d_6$) δ ppm 2.20 (s, 3 H) 3.60 (s, 3 H) 3.64 (q, J=5.4 Hz, 2 H) 3.77-3.88 (m, 5 H) 3.97 (s, 3 H) 4.78 (t, J=5.4 Hz, 1 H) 5.70 (t, J=2.0 Hz, 1 H) 5.92 (d, J=2.0 Hz, 2 H) 6.11 (d, J=7.9 Hz, 1 H) 6.33 (d, J=7.9 Hz, 1 H) 6.92 (s, 1 H) 6.95 (dd, J=8.2, 1.9 Hz, 1 H) 7.09 (d, J=1.9 Hz, 1 H) 7.35 (d, J=8.2 Hz, 1 H) 7.88 (s, 1 H) 8.23 (s, 1 H) 11.75 (br. s., 1 H)

LC/MS (method LC-C): $R_t$ 3.04 min, MH$^+$ 525

$[\alpha]_D^{20}$: -121.9° (c 0.3855, DMF)

Chiral SFC (method SFC-B): $R_t$ 3.75 min, MH$^+$ 525, chiral purity 99.86%.

Example 7

Synthesis of 2-(4-chloro-2-methoxyphenyl)-1-(5-fluoro-6-methoxy-1H-indol-3-yl)-2-((3-(2-hydroxyethoxy)-5-methoxyphenyl)amino)ethanone (Compound 7) and Chiral Separation into Enantiomers 7A and 7B

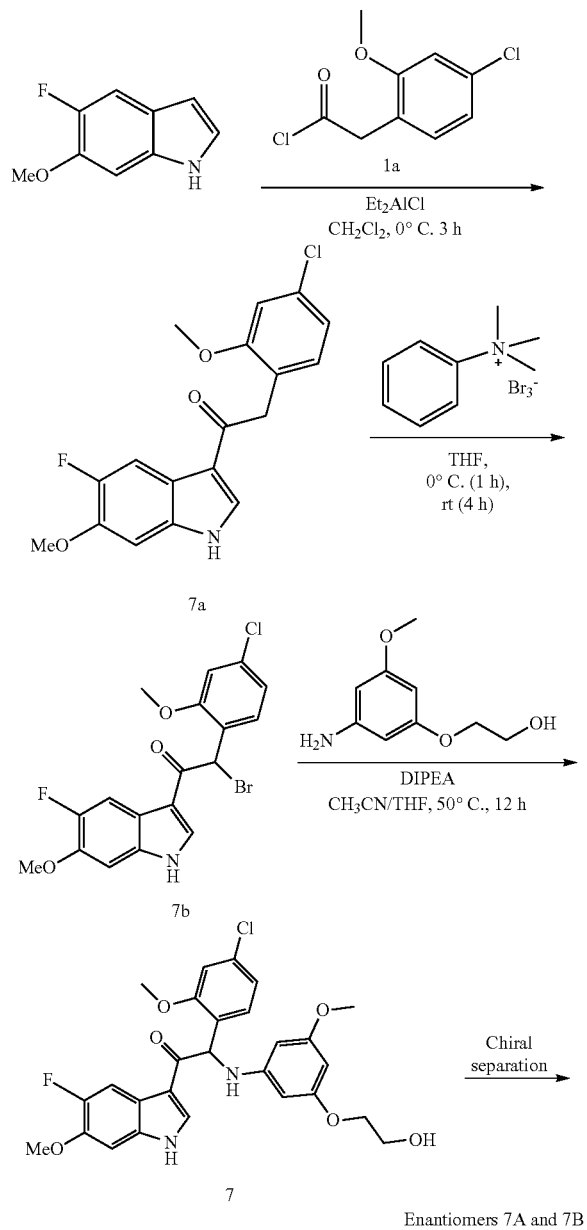

Synthesis of Intermediate 7a:

Diethylaluminum chloride 1M in hexane (15.7 mL, 15.7 mmol) was added dropwise at 0° C. to a solution of 5-fluoro-6-methoxy-1H-indole [CAS 1211595-72-0] (2 g, 12.1 mmol) in CH$_2$Cl$_2$ (50 mL). After 30 min at 0° C., a solution of 2-(4-chloro-2-methoxyphenyl)acetyl chloride 1a (3.2 g, 14.6 mmol, synthesis: see example 1) in CH$_2$Cl$_2$ (50 mL) was added slowly at 0° C. The reaction was stirred at 0° C. for 3 h. Ice-water was added and the precipitate was filtered off, washed with water and the minimum of CH$_2$Cl$_2$. The solid was dried under vacuum to give 2-(4-chloro-2-methoxyphenyl)-1-(5-fluoro-6-methoxy-1H-indol-3-yl)ethanone 7a (2.82 g).

Synthesis of Intermediate 7b:

At 0° C., a solution of phenyltrimethylammonium tribromide [CAS 4207-56-1] (3.5 g, 8.1 mmol) in THF (20 mL) was added dropwise to a solution of 2-(4-chloro-2-methoxyphenyl)-1-(5-fluoro-6-methoxy-1H-indol-3-yl)ethanone 7a (2.82 g, 8.1 mmol) in THF (46 mL). The mixture was stirred at 0° C. for 1 h and at room temperature for 4 h. The precipitate was filtered off and washed with EtOAc. The filtrate was concentrated under reduced pressure. The residue was dissolved in EtOAc, washed with water. The organic phase was dried over MgSO$_4$, filtered and the solvent was evaporated under reduced pressure. The residue was taken up with the minimum of EtOAc. The precipitate was filtered off and dried under vacuum to give 2-bromo-2-(4-chloro-2-methoxyphenyl)-1-(5-fluoro-6-methoxy-1H-indol-3-yl)ethanone 7b (2.5 g).

Synthesis of Compound 7 and Chiral Separation into Enantiomers 7A and 7B:

A mixture of 2-bromo-2-(4-chloro-2-methoxyphenyl)-1-(5-fluoro-6-methoxy-1H-indol-3-yl)ethanone 7b (2.4 g, 5.6 mmol), 2-(3-amino-5-methoxyphenoxy)ethanol [CAS 725237-16-1] (1.5 g, 8.2 mmol) and diisopropylethylamine (1.45 mL, 8.4 mmol) in CH$_3$CN/THF (1/1) (48 mL) was stirred at 50° C. for 12 h. The mixture was concentrated under reduced pressure. The residue was diluted with EtOAc, washed with 1N HCl and water. The organic layer was separated, dried over MgSO$_4$, filtered and the solvent was evaporated under reduced pressure. The residue was purified by column chromatography on silica gel (15-40 µm, 80 g in CH$_2$Cl$_2$/MeOH (99.5/0.5)). The pure fractions were collected and evaporated under reduced pressure. A small amount was solidified from Et$_2$O/CH$_3$CN to give an analytical sample of 2-(4-chloro-2-methoxyphenyl)-1-(5-fluoro-6-methoxy-1H-indol-3-yl)-2-((3-(2-hydroxyethoxy)-5-methoxyphenyl)amino)ethanone (Compound 7) as a racemic mixture.

The Enantiomers of Compound 7 (1.6 g) were separated via Preparative Chiral SFC (Stationary phase: Chiralpak® IC 5 µm 250×30 mm, Mobile phase: 55% CO$_2$, 45% MeOH) to give 680 mg of the first eluted enantiomer and 720 mg of the second eluted enantiomer. The first eluted enantiomer was solidified from CH$_3$CN/Et$_2$O to afford Enantiomer 7A (603 mg) as an amorphous white powder. The second eluted enantiomer was solidified from CH$_3$CN/Et$_2$O to afford Enantiomer 7B (505 mg) as an amorphous white powder.

Compound 7:

$^1$H NMR (400 MHz, DMSO-d$_6$) δ ppm 3.60 (s, 3 H) 3.62-3.67 (m, 2 H) 3.74-3.88 (m, 5 H) 3.96 (s, 3 H) 4.77 (t, J=5.3 Hz, 1 H) 5.66-5.75 (m, 1 H) 5.92 (d, J=1.8 Hz, 2 H) 6.12 (d, J=8.1 Hz, 1 H) 6.37 (d, J=8.1 Hz, 1 H) 6.96 (dd, J=8.1, 1.8 Hz, 1 H) 7.09 (d, J=1.8 Hz, 1 H) 7.14 (d, J=7.6 Hz, 1 H) 7.35 (d, J=8.1 Hz, 1H) 7.81 (d, J=11.6 Hz, 1 H) 8.33 (s, 1 H) 11.94 (br. s., 1 H)

LC/MS (method LC-C): $R_t$ 2.90 min, MH$^+$ 529

Enantiomer 7A:

$^1$H NMR (500 MHz, DMSO-d$_6$) δ ppm 3.60 (s, 3 H) 3.64 (q, J=5.5 Hz, 2 H) 3.76-3.88 (m, 5 H) 3.96 (s, 3 H) 4.79 (t, J=5.5 Hz, 1 H) 5.71 (t, J=1.9 Hz, 1 H) 5.92 (d, J=1.9 Hz, 2 H) 6.12 (d, J=8.2 Hz, 1 H) 6.39 (d, J=8.2 Hz, 1 H) 6.96 (dd, J=8.2, 2.0 Hz, 1 H) 7.09 (d, J=1.9 Hz, 1 H) 7.14 (d, J=7.6

Hz, 1 H) 7.35 (d, J=8.2 Hz, 1 H) 7.81 (d, J=11.7 Hz, 1 H) 8.34 (s, 1 H) 11.95 (br. s., 1 H)

LC/MS (method LC-C): $R_t$ 2.90 min, MH+ 529

$[\alpha]_D^{20}$: +86.2° (c 0.232, DMF)

Chiral SFC (method SFC-B): $R_t$ 2.28 min, MH+ 529, chiral purity 100%.

Enantiomer 7B:

$^1$H NMR (500 MHz, DMSO-$d_6$) δ ppm 3.60 (s, 3 H) 3.64 (q, J=5.5 Hz, 2 H) 3.76-3.88 (m, 5 H) 3.96 (s, 3 H) 4.79 (t, J=5.5 Hz, 1 H) 5.71 (t, J=1.9 Hz, 1 H) 5.92 (d, J=1.9 Hz, 2 H) 6.12 (d, J=8.2 Hz, 1 H) 6.39 (d, J=8.2 Hz, 1 H) 6.96 (dd, J=8.2, 1.9 Hz, 1 H) 7.09 (d, J=1.9 Hz, 1 H) 7.14 (d, J=7.6 Hz, 1 H) 7.35 (d, J=8.2 Hz, 1 H) 7.81 (d, J=12.0 Hz, 1 H) 8.34 (s, 1 H) 11.95 (br. s., 1 H)

LC/MS (method LC-C): $R_t$ 2.90 min, MH+ 529

$[\alpha]_D^{20}$: −88.7° (c 0.3, DMF)

Chiral SFC (method SFC-B): $R_t$ 4.04 min, MH+ 529, chiral purity 100%.

Example 8

Synthesis of 2-(4-chloro-2-methoxyphenyl)-1-(5-fluoro-7-methyl-1H-indol-3-yl)-2-((3-(2-hydroxyethoxy)-5-methoxyphenyl)amino)ethanone (Compound 8) and Chiral Separation into Enantiomers 8A and 8B

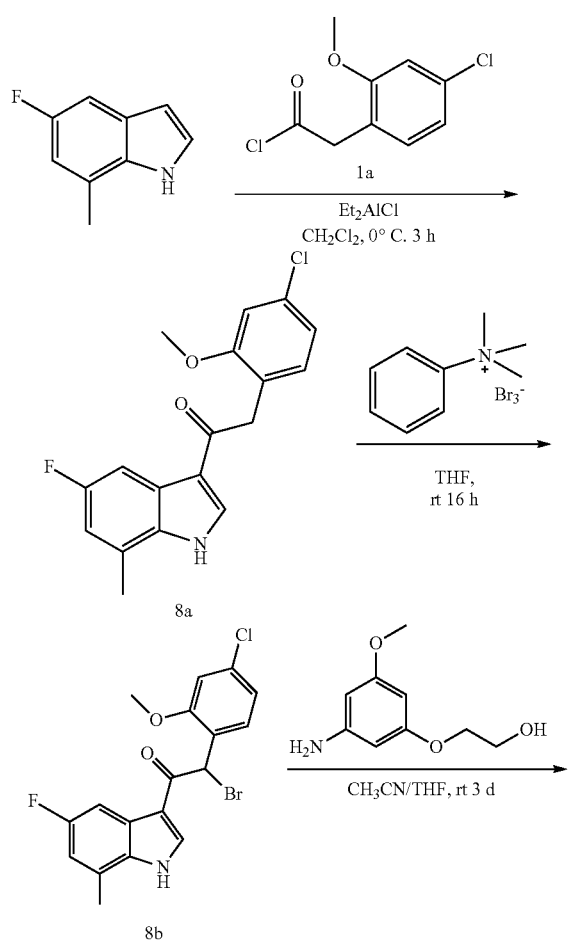

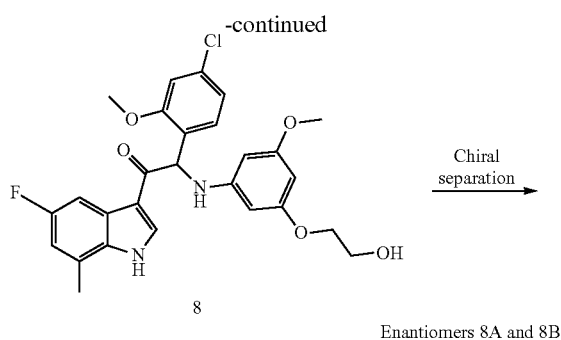

Enantiomers 8A and 8B

Synthesis of Intermediate 8a:

Diethylaluminum chloride 1M in hexane (15.0 mL, 15.0 mmol) was added dropwise at 0° C. to a solution of 5-fluoro-7-methyl-1H-indole [CAS 1082041-52-8] (1.49 g, 10.0 mmol) in $CH_2Cl_2$ (20 mL). After 30 min at 0° C., a solution of 2-(4-chloro-2-methoxyphenyl)acetyl chloride 1a (3.28 g, 15.0 mmol, synthesis: see Example 1) in $CH_2Cl_2$ (10 mL) was added slowly at 0° C. The reaction was stirred at 0° C. for 3 h. 1M Rochelle salt solution was added and the reaction mixture was stirred at room temperature for 30 min. The formed solids were filtered off and partitioned between EtOAc and 1N HCl. The phases were separated. The aqueous layer was extracted with EtOAc. The organic phases were combined, washed with brine, dried over $MgSO_4$, filtered and concentrated under reduced pressure to give 2-(4-chloro-2-methoxyphenyl)-1-(5-fluoro-7-methyl-1H-indol-3-yl)ethanone 8a (2.03 g).

Synthesis of Intermediate 8b:

A solution of phenyltrimethylammonium tribromide [CAS 4207-56-1] (2.53 g, 6.72 mmol) in THF (10 mL) was added dropwise at 0° C. to a solution of 2-(4-chloro-2-methoxyphenyl)-1-(5-fluoro-7-methyl-1H-indol-3-yl)ethanone 8a (2.03 g, 6.11 mmol) in THF (50 mL). The reaction mixture was stirred at room temperature overnight. The precipitate was filtered off and washed with EtOAc. The filtrate was concentrated under reduced pressure. The residue was taken up with a minimum of acetonitrile. The precipitate was filtered off, washed with acetonitrile and dried under vacuum to give 2-bromo-2-(4-chloro-2-methoxyphenyl)-1-(5-fluoro-7-methyl-1H-indol-3-yl)ethanone 8b (2.00 g).

Synthesis of Compound 8 and Chiral Separation into Enantiomers 8A and 8B: A mixture of 2-bromo-2-(4-chloro-2-methoxyphenyl)-1-(5-fluoro-7-methyl-1H-indol-3-yl)ethanone 8b (1.70 g, 4.14 mmol) and 2-(3-amino-5-methoxyphenoxy)ethanol [CAS 725237-16-1] (2.28 g, 12.4 mmol) in THF (10 mL) and $CH_3CN$ (10 mL) was stirred at room temperature for 3 days. The reaction mixture was concentrated under reduced pressure. The residue was partitioned between EtOAc and 1N HCl. The phases were separated. The organic phase was washed twice with 1N HCl, with an aqueous saturated $NaHCO_3$ solution and brine, dried over $MgSO_4$, filtered and concentrated under reduced pressure. The residue was taken up with a minimum amount of acetonitrile. The precipitate was filtered off and dried under vacuum to give 2-(4-chloro-2-methoxyphenyl)-1-(5-fluoro-7-methyl-1H-indol-3-yl)-2-((3-(2-hydroxyethoxy)-5-methoxyphenyl)amino)ethan-one (Compound 8, 1.23 g) as a racemic mixture.

The enantiomers of Compound 8 (1.17 g) were separated via Normal Phase Chiral separation (Stationary phase: Daicel Chiralpak® OD-H, Mobile phase: 80% heptane, 20% ethanol). The first eluted product was further purified by flash chromatography (Stationary phase: Biotage® Grace Reveleris Silica 12 g, Mobile phase: heptane/EtOAc/EtOH gradient 100/0/0 to 40/45/15). The pure fractions were combined and evaporated. The product was crystallized overnight from a mixture of MeOH (4 mL) and water (1 mL), filtered off, washed with MeOH (3×) and dried under vacuum at 50° C. to provide Enantiomer 8A (37 mg). The second eluted product was further purified by Flash Chromatography (Stationary phase: Biotage® Grace Reveleris Silica 12 g, Mobile phase: heptane/EtOAc/EtOH gradient 100/0/0 to 40/45/15). The pure fractions were combined and evaporated. The product was crystallized from a mixture of MeOH and $H_2O$, filtered off, washed with MeOH and dried under vacuum at 50° C. to provide Enantiomer 8B (177 mg).

Compound 8:

$^1$H NMR (300 MHz, DMSO-$d_6$) δ ppm 2.48 (s, 3 H) 3.56-3.71 (m, 5 H) 3.74-3.92 (m, 2 H) 3.97 (s, 3 H) 4.79 (t, J=5.5 Hz, 1 H) 5.72 (s, 1 H) 5.95 (d, J=1.9 Hz, 2 H) 6.17 (d, J=7.9 Hz, 1 H) 6.40 (d, J=8.3 Hz, 1 H) 6.87-7.01 (m, 2 H) 7.10 (d, J=1.9 Hz, 1 H) 7.36 (d, J=8.3 Hz, 1 H) 7.65 (dd, J=9.8, 2.3 Hz, 1 H) 8.46 (s, 1 H) 12.22 (br. s., 1 H)

LC/MS (method LC-D): $R_t$ 1.52 min, MH$^+$ 513

Enantiomer 8A:

$^1$H NMR (400 MHz, DMSO-$d_6$) δ ppm 3.61 (s, 3 H) 3.64 (q, J=5.2 Hz, 2 H) 3.77 (s, 3 H) 3.78-3.89 (m, 2 H) 3.97 (s, 3 H) 4.77 (t, J=5.6 Hz, 1 H) 5.71 (t, J=2.1 Hz, 1 H) 5.93 (d, J=2.0 Hz, 2 H) 6.12 (d, J=7.9 Hz, 1 H) 6.35 (d, J=7.9 Hz, 1 H) 6.82 (dd, J=8.7, 2.3 Hz, 1 H) 6.91-7.01 (m, 2 H) 7.09 (d, J=2.0 Hz, 1 H) 7.36 (d, J=8.1 Hz, 1 H) 8.01 (d, J=8.6 Hz, 1 H) 8.29 (d, J=2.9 Hz, 1 H) 11.81 (br d, J=2.4 Hz, 1 H)

LC/MS (method LC-A): $R_t$ 1.12 min, MH$^+$ 513

$[α]_D^{20}$: −83.8° (c 0.4725, DMF)

Chiral SFC (method SFC-G): $R_t$ 2.32 min, MH$^+$ 513, chiral purity 100%

Enantiomer 8B:

$^1$H NMR (400 MHz, DMSO-$d_6$) δ ppm 2.47 (s, 3 H) 3.61 (s, 3 H) 3.65 (q, J=5.2 Hz, 2 H) 3.77-3.90 (m, 2 H) 3.97 (s, 3 H) 4.77 (t, J=5.6 Hz, 1 H) 5.72 (t, J=2.1 Hz, 1 H) 5.95 (d, J=2.0 Hz, 2 H) 6.16 (d, J=8.1 Hz, 1 H) 6.37 (d, J=7.9 Hz, 1 H) 6.92 (dd, J=10.1, 2.0 Hz, 1 H) 6.96 (dd, J=8.3, 1.9 Hz, 1 H) 7.10 (d, J=1.8 Hz, 1H) 7.36 (d, J=8.4 Hz, 1 H) 7.65 (dd, J=9.7, 2.4 Hz, 1 H) 8.45 (d, J=3.5 Hz, 1 H) 12.20 (br d, J=2.9 Hz, 1 H)

LC/MS (method LC-A): $R_t$ 1.14 min, MH$^+$ 513

$[α]_D^{20}$: +86.6° (c 0.4805, DMF)

Chiral SFC (method SFC-G): $R_t$ 1.44 min, MH$^+$ 513, chiral purity 100%

Example 9

Synthesis of 2-(4-chloro-2-methoxyphenyl)-1-(5,6-difluoro-1H-indol-3-yl)-2-((3-(2-hydroxyethoxy)-5-methoxyphenyl)amino)ethanone (Compound 9) and Chiral Separation into Enantiomers 9A and 9B

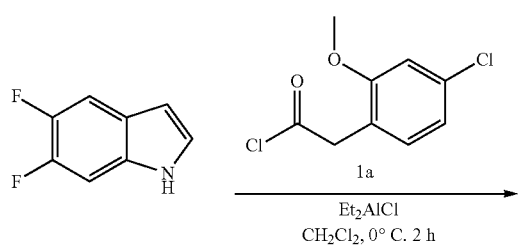

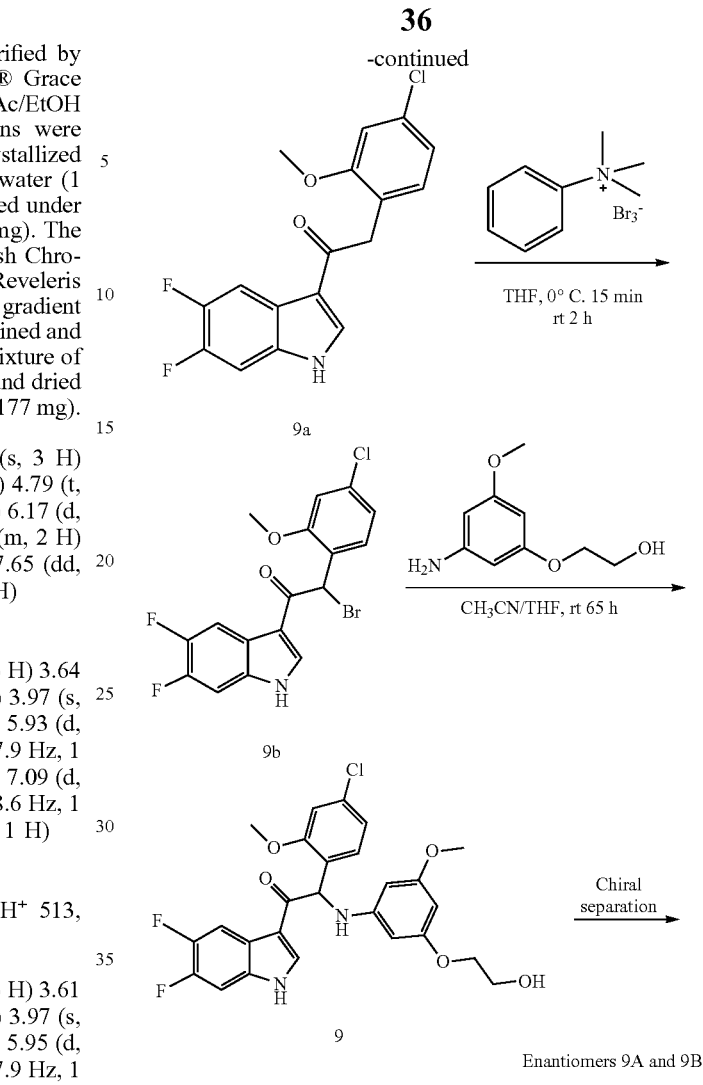

Enantiomers 9A and 9B

Synthesis of Intermediate 9a:

Diethylaluminum chloride 1M in hexane (14.9 mL, 14.9 mmol) was added dropwise at 0° C. to a solution of 5,6-difluoro-1H-indole [CAS 169674-01-5] (1.50 g, 9.8 mmol) in $CH_2Cl_2$ (20 mL). After 30 min at 0° C., a solution of 2-(4-chloro-2-methoxyphenyl)acetyl chloride 1a (3.22 g, 14.7 mmol, synthesis: see Example 1) in $CH_2Cl_2$ (20 mL) was added slowly at 0° C. The reaction was stirred at 0° C. for 2 h. 1M Rochelle salt solution was added and the reaction mixture was vigorously stirred at room temperature for 2 h. The precipitate was filtered off and partitioned between EtOAc and 1N HCl. The phases were separated. The aqueous layer was extracted twice with EtOAc. The organic phases were combined, dried over $MgSO_4$, filtered and concentrated under reduced pressure. The residue was taken up with a minimum of acetonitrile. The precipitate was filtered off and dried under vacuum to give 2-(4-chloro-2-methoxyphenyl)-1-(5,6-difluoro-1H-indol-3-yl)ethanone 9a (2.73 g).

Synthesis of Intermediate 9b:

A solution of phenyltrimethylammonium tribromide [CAS 4207-56-1] (3.36 g, 8.94 mmol) in THF (50 mL) was added dropwise at 0° C. to a solution of 2-(4-chloro-2-methoxyphenyl)-1-(5,6-difluoro-1H-indol-3-yl)-2-(4-chloro-2-methoxyphenyl)ethanone 9a (2.73 g, 8.13 mmol) in THF (80 mL). The reaction mixture was stirred at 0° C.

for 15 min and at room temperature for 2 h. The precipitate was filtered off and washed with EtOAc. The filtrate was concentrated under reduced pressure. The residue was taken up with a minimum of acetonitrile. The precipitate was filtered off and dried under vacuum to give 2-bromo-2-(4-chloro-2-methoxyphenyl)-1-(5,6-difluoro-1H-indol-3-yl)ethanone 9b (3.00 g).

Synthesis of Compound 9 and Chiral Separation into Enantiomers 9A and 9B:

A mixture of 2-bromo-2-(4-chloro-2-methoxyphenyl)-1-(5,6-difluoro-1H-indol-3-yl)ethanone 9b (1.80 g, 4.34 mmol) and 2-(3-amino-5-methoxyphenoxy)ethanol [CAS 725237-16-1] (2.39 g, 13.0 mmol) in THF (9 mL) and $CH_3CN$ (9 mL) was stirred at room temperature for 65 h. 1N HCl was added and the reaction mixture was extracted with EtOAc. The phases were separated. The organic phase was washed with 1N HCl, dried over $MgSO_4$, filtered and concentrated under reduced pressure. The residue was purified by flash chromatography on silica gel using a gradient of EtOAc (15% to 70%) in dichloromethane. The pure fractions were combined and concentrated under reduced pressure to afford 2-(4-chloro-2-methoxyphenyl)-1-(5,6-difluoro-1H-indol-3-yl)-2-((3-(2-hydroxyethoxy)-5-methoxyphenyl)amino)ethanone (Compound 9, 1.20 g) as a racemic mixture. The impure fractions were combined and purified by flash chromatography on silica gel using a gradient of ethyl acetate (15% to 70%) in dichloromethane to afford a second batch of Compound 9 (0.290 g) as a racemic mixture.

The enantiomers of Compound 9 (1.4 g) were separated via Normal Phase Chiral separation (Stationary phase: Daicel Chiralpak® OD-H, Mobile phase: 80% heptane, 20% ethanol). The first eluted product was further purified by flash chromatography (Stationary phase: Biotage® Grace Reveleris Silica 12 g, Mobile phase: $CH_2Cl_2$/MeOH gradient from 100/0 to 90/10). The pure fractions were combined, evaporated and co-evaporated with MeOH. The residue was lyophilized from a solvent mixture of $CH_3CN$ (4.5 mL) and water (2.5 mL) and dried under vacuum at 45° C. to provide Enantiomer 9A (409 mg). The second eluted product was further purified by flash chromatography (Stationary phase: Biotage® Grace Reveleris Silica 12 g, Mobile phase: $CH_2Cl_2$/MeOH gradient from 100/0 to 90/10). The pure fractions were combined, evaporated and co-evaporated with MeOH. The residue was lyophilized from a solvent mixture of $CH_3CN$ (5 mL) and water (3 mL) and dried under vacuum at 45° C. to provide Enantiomer 9B (388 mg).

Compound 9:

$^1$H NMR (300 MHz, DMSO-$d_6$) δ ppm 3.61 (s, 3 H) 3.62-3.70 (m, 2 H) 3.75-3.90 (m, 2 H) 3.95 (s, 3 H) 4.79 (t, J=5.6 Hz, 1 H) 5.72 (t, J=2.1 Hz, 1 H) 5.93 (d, J=2.0 Hz, 1 H) 6.15 (d, J=8.1 Hz, 1 H) 6.42 (d, J=8.1 Hz, 1 H) 6.97 (dd, J=8.2, 2.2 Hz, 1 H) 7.10 (d, J=2.0 Hz, 1 H) 7.35 (d, J=8.3 Hz, 1 H) 7.54 (dd, J=10.8, 7.0 Hz, 1 H) 7.99 (dd, J=11.2, 8.2 Hz, 1 H) 8.48 (s, 1 H) 12.19 (br. s., 1 H)

LC/MS (method LC-D): $R_t$ 1.44 min, MH$^+$ 517

Enantiomer 9A:

$^1$H NMR (400 MHz, DMSO-$d_6$) δ ppm 3.61 (s, 3 H) 3.64 (q, J=5.2 Hz, 2 H) 3.77-3.89 (m, 2 H) 3.95 (s, 3 H) 4.77 (t, J=5.5 Hz, 1 H) 5.72 (t, J=2.1 Hz, 1 H) 5.93 (d, J=2.0 Hz, 2 H) 6.14 (d, J=8.1 Hz, 1 H) 6.39 (d, J=8.1 Hz, 1 H) 6.97 (dd, J=8.4, 2.0 Hz, 1 H) 7.09 (d, J=2.0 Hz, 1 H) 7.35 (d, J=8.1 Hz, 1 H) 7.53 (dd, J=10.8, 7.0 Hz, 1 H) 7.99 (dd, J=11.2, 8.1 Hz, 1 H) 8.47 (s, 1H) 12.16 (br s, 1H)

LC/MS (method LC-A): $R_t$ 1.15 min, MH$^+$ 517

$[α]_D^{20}$: −98.9° (c 0.445, DMF)

Chiral SFC (method SFC-G): $R_t$ 1.92 min, MH$^+$ 517, chiral purity 100%

Enantiomer 9B:

$^1$H NMR (400 MHz, DMSO-$d_6$) δ ppm 3.61 (s, 3 H) 3.64 (q, J=5.2 Hz, 2 H) 3.75-3.91 (m, 2 H) 3.95 (s, 3 H) 4.77 (t, J=5.6 Hz, 1 H) 5.72 (t, J=2.1 Hz, 1 H) 5.93 (d, J=2.2 Hz, 2 H) 6.14 (d, J=8.1 Hz, 1 H) 6.39 (d, J=8.1 Hz, 1 H) 6.97 (dd, J=8.1, 2.0 Hz, 1 H) 7.09 (d, J=2.0 Hz, 1 H) 7.35 (d, J=8.1 Hz, 1 H) 7.53 (dd, J=10.8, 7.0 Hz, 1 H) 7.99 (dd, J=11.1, 8.3 Hz, 1 H) 8.47 (s, 1 H) 12.16 (br s, 1H)

LC/MS (method LC-A): $R_t$ 1.15 min, MH$^+$ 517

$[α]_D^{20}$: +98.9° (c 0.555, DMF)

Chiral SFC (method SFC-G): $R_t$ 1.36 min, MH$^+$ 517, chiral purity 100%

Example 10

Synthesis of 2-(4-chloro-2-methoxyphenyl)-1-(7-fluoro-5-methyl-1H-indol-3-yl)-2-((3-(2-hydroxyethoxy)-5-methoxyphenyl)amino)ethanone (Compound 10) and Chiral Separation into Enantiomers 10A and 10B

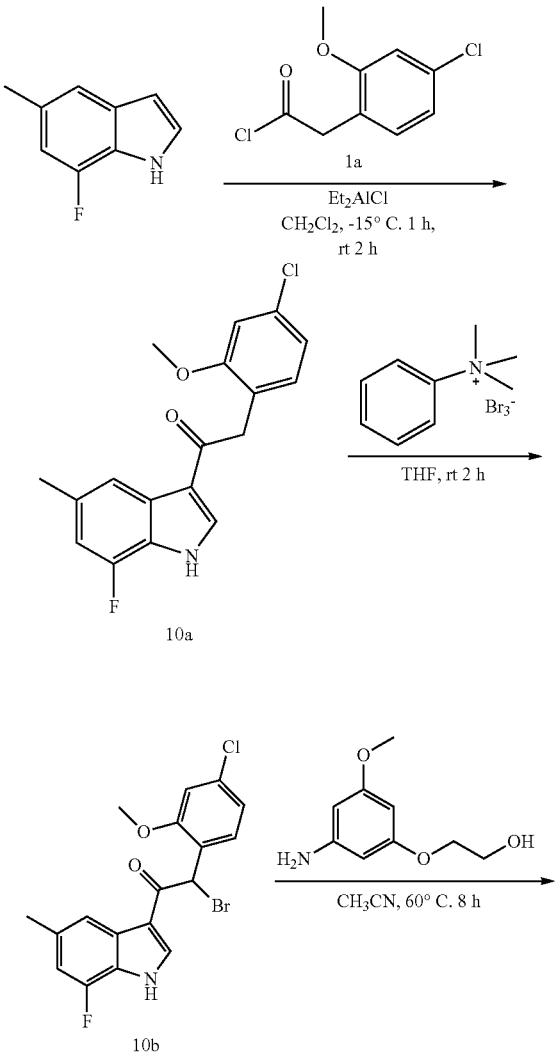

-continued

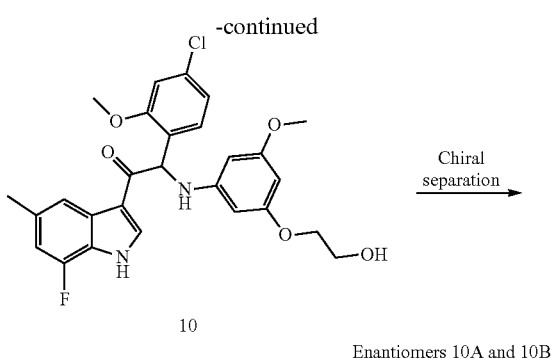

10

Enantiomers 10A and 10B

Synthesis of Intermediate 10a:

Diethylaluminum chloride 1M in hexane (16 mL, 16 mmol) was added dropwise at −15° C. to a solution of 7-fluoro-5-methyl-1H-indole [CAS 442910-91-0] (1.59 g, 10.7 mmol) in $CH_2Cl_2$ (150 mL) under $N_2$ flow. After 15 min at −15° C., a solution of 2-(4-chloro-2-methoxyphenyl) acetyl chloride 1a (3.27 g, 14.9 mmol, synthesis: see Example 1) in $CH_2Cl_2$ (50 mL) was added slowly at −15° C. The reaction was stirred at −15° C. for 1 h and at room temperature for 2 h. The reaction mixture was poured out into a stirred ice/Rochelle salt mixture. The solids were removed from the reaction mixture by filtration over a short pad of dicalite® and the filter cake was rinsed several times with THF. The layers were separated and the aqueous layer was extracted with THF. The combined organic layers were washed with brine, water, dried on $MgSO_4$, filtered, and evaporated under reduced pressure. The solid residue was suspended in $CH_2Cl_2$ (10 mL). The solids were filtered off, washed with a small amount of $CH_2Cl_2$ and dried under vacuum at 50° C. to give 2-(4-chloro-2-methoxyphenyl)-1-(7-fluoro-5-methyl-1H-indol-3-yl)ethanone 10a (2.22 g).

Synthesis of Intermediate 10b:

A solution of phenyltrimethylammonium tribromide [CAS 4207-56-1] (2.77 g, 7.36 mmol) in THF (50 mL) was added dropwise at 0° C. to a solution of 2-(4-chloro-2-methoxyphenyl)-1-(7-fluoro-5-methyl-1H-indol-3-yl)ethanone 10a (2.22 g, 6.7 mmol) in THF (150 mL). The reaction mixture was stirred at room temperature for 2 h. The precipitate was filtered off and washed with THF. The filtrate was concentrated under reduced pressure. The residue was taken up with a minimum of $CH_2Cl_2$. The precipitate was filtered off, washed with $CH_2Cl_2$ (2×) and dried under vacuum at 50° C. to give 2-bromo-2-(4-chloro-2-methoxyphenyl)-1-(7-fluoro-5-methyl-1H-indol-3-yl)ethanone 10b (2.55 g).

Synthesis of Compound 10 and Chiral Separation into Enantiomers 10A and 10B:

A mixture of 2-bromo-2-(4-chloro-2-methoxyphenyl)-1-(7-fluoro-5-methyl-1H-indol-3-yl)ethanone 10b (2 g, 4.87 mmol), 2-(3-amino-5-methoxyphenoxy)ethanol [CAS 725237-16-1] (1.6 g, 7.3 mmol) and diisopropylethylamine (1.26 mL, 7.3 mmol) in $CH_3CN$ (100 mL) was stirred at room temperature for 20 h, at 60° C. for 8 h and again at room temperature for 16 h. The solvent was evaporated under reduced pressure. The residue was dissolved in $CH_2Cl_2$ (50 mL), washed with 0.5 M HCl (50 mL) and water (50 mL), dried over $MgSO_4$, filtered and evaporated. The residue was purified by column chromatography (Stationary phase: Biotage® Grace Reveleris Silica 120 g, Mobile phase: EtOAc/heptane gradient from 0/100 to 60/40). The fractions containing product were combined, evaporated and dried at 50° C. under vacuum to give 2-(4-chloro-2-methoxyphenyl)-1-(7-fluoro-5-methyl-1H-indol-3-yl)-2-((3-(2-hydroxyethoxy)-5-methoxyphenyl)amino)ethanone (Compound 10, 1.3 g) as a white solid.

The enantiomers of Compound 10 (1.3 g) were separated via Normal Phase Chiral separation (Stationary phase: AD-H, Mobile phase: 70% ethanol, 30% methanol) to provide 637 mg of the first eluted enantiomer and 628 mg of the second eluted enantiomer. The first eluted product was crystallized from a MeOH/water mixture. The solids were filtered off and washed with a MeOH/water (1/1) mixture to provide Enantiomer 10A (302 mg) as a white amorphous powder. The second eluted product was further purified by flash chromatography (Stationary phase: Biotage® Grace Reveleris Silica 40 g, Mobile phase: MeOH/$CH_2Cl_2$ gradient from 0/100 to 2/98). The fractions containing product were combined and evaporated to provide Enantiomer 10B (335 mg) as a white amorphous powder.

Compound 10:

$^1$H NMR (400 MHz, DMSO-$d_6$) δ ppm 2.38 (s, 3 H) 3.61 (s, 3 H) 3.62-3.67 (m, 2 H) 3.77-3.89 (m, 2 H) 3.95 (s, 3 H) 4.77 (t, J=5.5 Hz, 1 H) 5.72 (t, J=2.0 Hz, 1 H) 5.94 (d, J=2.0 Hz, 2 H) 6.15 (d, J=8.1 Hz, 1 H) 6.34 (d, J=8.1 Hz, 1 H) 6.90 (d, J=12.1 Hz, 1 H) 6.96 (dd, J=8.1, 2.0 Hz, 1 H) 7.09 (d, J=2.0 Hz, 1 H) 7.35 (d, J=8.4 Hz, 1 H) 7.77 (s, 1 H) 8.38 (s, 1 H) 12.46 (br s, 1 H)

LC/MS (method LC-A): $R_t$ 1.16 min, MH$^+$ 513

Enantiomer 10A:

$^1$H NMR (400 MHz, DMSO-$d_6$) δ ppm 2.38 (s, 3 H) 3.62 (s, 3 H) 3.66 (br t, J=4.8 Hz, 2 H) 3.77-3.92 (m, 2 H) 3.96 (s, 3 H) 4.78 (br s, 1 H) 5.73 (s, 1 H) 5.96 (s, 2 H) 6.17 (br d, J=7.9 Hz, 1 H) 6.35 (br d, J=8.1 Hz, 1 H) 6.91 (d, J=12.1 Hz, 1 H) 6.97 (dd, J=8.3, 1.4 Hz, 1 H) 7.10 (d, J=1.5 Hz, 1 H) 7.36 (d, J=8.4 Hz, 1 H) 7.79 (s, 1 H) 8.39 (s, 1 H) 12.47 (br s, 1 H)

LC/MS (method LC-A): $R_t$ 1.15 min, MH$^+$ 513

$[α]_D^{20}$: +132.3° (c 0.505, DMF)

Chiral SFC (method SFC-F): $R_t$ 2.13 min, MH$^+$ 513, chiral purity 100%

Enantiomer 10B:

$^1$H NMR (400 MHz, DMSO-$d_6$) δ ppm 2.38 (s, 3 H) 3.61 (s, 3 H) 3.63-3.68 (m, 2 H) 3.77-3.92 (m, 2 H) 3.96 (s, 3 H) 4.77 (br t, J=5.7 Hz, 1 H) 5.72 (t, J=2.0 Hz, 1 H) 5.95 (d, J=2.0 Hz, 2 H) 6.16 (d, J=7.9 Hz, 1 H) 6.35 (d, J=8.1 Hz, 1 H) 6.91 (d, J=12.1 Hz, 1 H) 6.97 (dd, J=8.4, 2.0 Hz, 1 H) 7.09 (d, J=2.0 Hz, 1 H) 7.36 (d, J=8.4 Hz, 1 H) 7.78 (s, 1 H) 8.39 (s, 1 H) 12.46 (br s, 1 H)

LC/MS (method LC-A): $R_t$ 1.15 min, MH$^+$ 513

$[α]_D^{20}$: −144.1° (c 0.4975, DMF)

Chiral SFC (method SFC-F): $R_t$ 3.13 min, MH$^+$ 513, chiral purity 100%

Example 11

Synthesis of 2-(4-chloro-2-methoxyphenyl)-1-(6,7-difluoro-1H-indol-3-yl)-2-((3-(2-hydroxyethoxy)-5-methoxyphenyl)amino)ethanone (Compound 11) and Chiral Separation into Enantiomers 11A and 11B

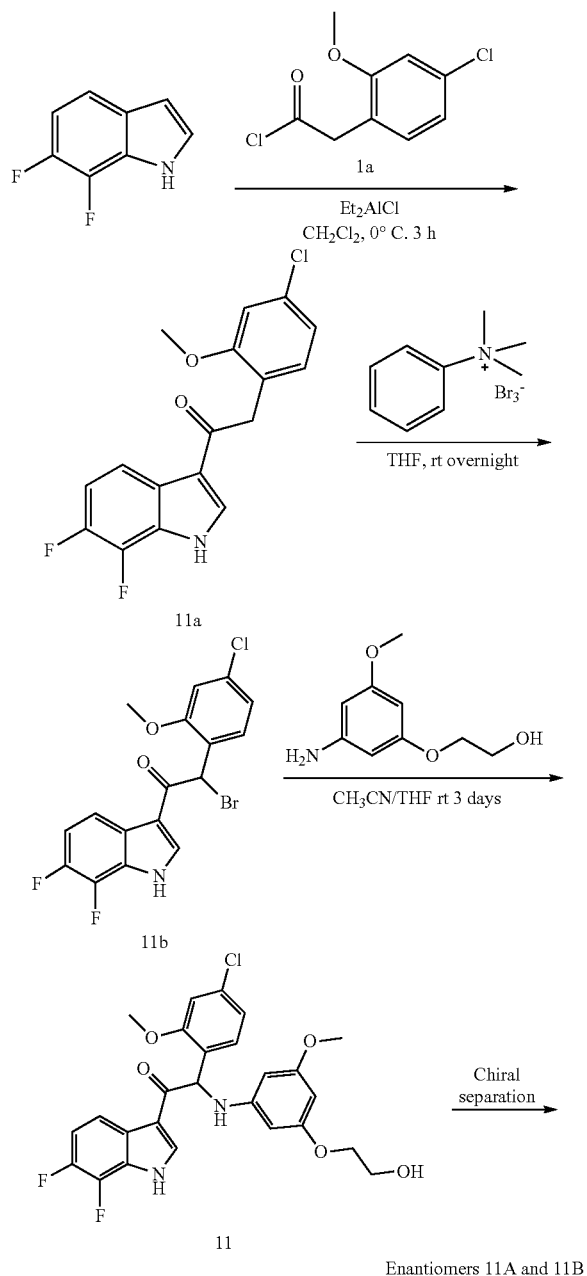

Synthesis of Intermediate 11a:

Diethylaluminum chloride 1M in hexane (15.0 mL, 15.0 mmol) was added dropwise at 0° C. to a solution of 6,7-difluoro-1H-indole [CAS 271780-84-8] (1.53 g, 10.0 mmol) in CH₂Cl₂ (20 mL). After 30 min at 0° C., a solution of 2-(4-chloro-2-methoxyphenyl)acetyl chloride 1a (3.28 g, 15.0 mmol, synthesis: see Example 1) in CH₂Cl₂ (10 mL) was added slowly at 0° C. The reaction was stirred at 0° C. for 3 h. 1M Rochelle salt solution was added and the reaction mixture was stirred at room temperature for 30 min. The solids were filtered off and partitioned between EtOAc and 1N HCl. The phases were separated. The aqueous layer was extracted with EtOAc. The organic phases were combined, washed with brine, dried over MgSO₄, filtered and concentrated under reduced pressure to give 2-(4-chloro-2-methoxyphenyl)-1-(6,7-difluoro-1H-indol-3-yl)ethanone 11a (2.36 g).

Synthesis of Intermediate 11b:

A solution of phenyltrimethylammonium tribromide [CAS 4207-56-1] (2.90 g, 7.02 mmol) in THF (10 mL) was added dropwise at 0° C. to a solution of 2-(4-chloro-2-methoxyphenyl)-1-(6,7-difluoro-1H-indol-3-yl)ethanone 11a (2.36 g, 7.02 mmol) in THF (50 mL). The reaction mixture was stirred at room temperature overnight. The precipitate was filtered off and washed with EtOAc. The filtrate was concentrated under reduced pressure. The residue was taken up with a minimum of acetonitrile. The precipitate was filtered off, washed with acetonitrile and dried under vacuum to give 2-bromo-2-(4-chloro-2-methoxyphenyl)-1-(6,7-difluoro-1H-indol-3-yl)ethanone 11b (2.34 g).

Synthesis of Compound 11 and Chiral Separation into Enantiomers 11A and 11B:

A mixture of 2-bromo-2-(4-chloro-2-methoxyphenyl)-1-(6,7-difluoro-1H-indol-3-yl)ethanone 11b (1.70 g, 4.14 mmol) and 2-(3-amino-5-methoxyphenoxy)ethanol [CAS 725237-16-1] (2.25 g, 12.3 mmol) in THF (10 mL) and CH₃CN (10 mL) was stirred at room temperature for 3 days. The reaction mixture was concentrated under reduced pressure. The residue was partitioned between EtOAc and 1N HCl. The phases were separated. The organic phase was washed twice with 1N HCl, with an aqueous saturated NaHCO₃ solution and brine, dried over MgSO₄, filtered and concentrated under reduced pressure. The residue was purified by flash chromatography on silica gel using a gradient of EtOAc (20% to 100%) in heptane. The fractions containing expected compound were combined and concentrated under reduced pressure. The residue was crystallized from a mixture of Et₂O, acetonitrile and heptane to afford 2-(4-chloro-2-methoxyphenyl)-1-(6,7-difluoro-1H-indol-3-yl)-2-((3-(2-hydroxyethoxy)-5-methoxyphenyl)amino)ethanone (Compound 11, 1.54 g) as a racemic mixture.

The enantiomers of Compound 11 (1.22 g) were separated via Preparative Chiral SFC (Stationary phase: Chiralcel® OD-H 5 μm 250×30 mm, Mobile phase: 55% CO₂, 45% MeOH) to give 550 mg of the first eluted enantiomer and 570 mg of the second eluted enantiomer. The first eluted enantiomer was solidified from CH₃CN/diisopropylether to afford Enantiomer 11A (487 mg). The second eluted enantiomer was solidified from CH₃CN/diisopropylether to afford Enantiomer 11B (460 mg). Both enantiomers occurred as amorphous powders.

Compound 11:
¹H NMR (300 MHz, DMSO-d₆) δ ppm 3.56-3.69 (m, 5 H) 3.75-3.90 (m, 2 H) 3.95 (s, 3 H) 4.79 (t, J=5.5 Hz, 1 H) 5.73 (s, 1 H) 5.95 (d, J=1.9 Hz, 2 H) 6.18 (d, J=8.3 Hz, 1 H) 6.41 (d, J=8.3 Hz, 1 H) 6.97 (dd, J=8.1, 1.7 Hz, 1 H) 7.10 (d, J=1.9 Hz, 1 H) 7.16-7.30 (m, 1 H) 7.36 (d, J=8.3 Hz, 1 H) 7.92 (dd, J=8.7, 4.5 Hz, 1 H) 8.50 (s, 1 H) 12.78 (br. s., 1 H)
LC/MS (method LC-D): R$_t$ 1.52 min, MH⁺ 517

Enantiomer 11A:
¹H NMR (500 MHz, DMSO-d₆) δ ppm 12.79 (br. s., 1 H) 8.50 (s, 1 H) 7.92 (dd, J=8.7, 4.3 Hz, 1 H) 7.36 (d, J=8.5 Hz, 1 H) 7.20-7.27 (m, 1 H) 7.10 (d, J=1.6 Hz, 1 H) 6.97 (dd, J=8.4, 1.7 Hz, 1 H) 6.42 (d, J=8.2 Hz, 1 H) 6.18 (d, J=8.2 Hz, 1 H) 5.95 (d, J=1.6 Hz, 2 H) 5.72 (s, 1 H) 4.79 (t, J=5.4 Hz, 1 H) 3.94 (s, 3 H) 3.78-3.89 (m, 2 H) 3.59-3.68 (m, 5 H)

LC/MS (method LC-C): $R_t$ 3.07 min, MH$^+$ 517

$[\alpha]_D^{20}$: −99.6° (c 0.2218, DMF)

Chiral SFC (method SFC-D): $R_t$ 1.80 min, MH$^+$ 517, chiral purity 100%.

Enantiomer 11B:

$^1$H NMR (500 MHz, DMSO-d$_6$) δ ppm 12.79 (br. s., 1 H) 8.50 (s, 1 H) 7.91 (dd, J=8.7, 4.3 Hz, 1 H) 7.36 (d, J=8.2 Hz, 1 H) 7.17-7.28 (m, 1 H) 7.10 (d, J=1.9 Hz, 1 H) 6.97 (dd, J=8.2, 1.9 Hz, 1 H) 6.41 (d, J=8.2 Hz, 1 H) 6.18 (d, J=8.2 Hz, 1 H) 5.95 (d, J=1.9 Hz, 2 H) 5.72 (t, J=1.9 Hz, 1 H) 4.79 (t, J=5.5 Hz, 1 H) 3.94 (s, 3 H) 3.77-3.88 (m, 2 H) 3.55-3.70 (m, 5 H)

LC/MS (method LC-C): $R_t$ 3.07 min, MH$^+$ 517

$[\alpha]_D^{20}$: +99.2° (c 0.2127, DMF)

Chiral SFC (method SFC-D): $R_t$ 3.38 min, MH$^+$ 517, chiral purity 100%.

Antiviral Activity of the Compounds of the Invention

DENV-2 Antiviral Assay

The antiviral activity of all the compounds of the invention was tested against DENV-2 16681 strain which was labeled with enhanced green fluorescent protein (eGPF). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 µL was added to 384-well plates (2500 cells/well), which already contain the antiviral compounds. Typically, these plates contain a 4-fold serial dilution of 9 dilution steps of the test compound at 200 times the final concentration in 100% DMSO (200 nL). In addition, each compound concentration is tested in quadruplicate (final concentration range: 25 µM-0.00038 µM). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 µL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% CO$_2$) until the next day. Then, DENV-2 strain 16681, labeled with eGFP, was added at a multiplicity of infection (MOI) of 0.5. Therefore, 15 µL of virus suspension was added to all the wells containing test compound and to the wells assigned as virus control. In parallel, 15 µL of culture medium was added to the medium and cell controls. Next, the plates were incubated for 3 days in a fully humidified incubator (37° C., 5% CO$_2$). At the day of the read out, the eGFP fluorescence was measured using an automated fluorescence microscope at 488 nm (blue laser). Using an in-house LIMS system, inhibition dose response curves for each compound were calculated and the half maximal effective concentration (EC$_{50}$) was determined. Therefore, the percent inhibition (I) for every test concentration is calculated using the following formula: I=100*(S$_T$−S$_{CC}$)/(S$_{VC}$−S$_{CC}$); S$_T$, S$_{CC}$ and S$_{VC}$ are the amount of eGFP signal in the test compound, cell control and virus control wells, respectively. The EC$_{50}$ represents the concentration of a compound at which the virus replication is inhibited with 50%, as measured by a 50% reduction of the eGFP fluorescent intensity compared to the virus control. The EC$_{50}$ is calculated using linear interpolation (Table 1).

In parallel, the toxicity of the compounds was assessed on the same plates. Once the read-out for the eGFP signal was done, 10 µL of resazurin, a cell viability stain, was added to all wells of the 384-well plates. The resazurin assay is based on the reduction of the blue resazurin by NADH, produced by the cells, into the highly fluorescent product, resorufin. The formation of pink fluorescent resorufin is directly related to the number of viable cells in the well. The plates were incubated for an additional 5 hours in a fully humidified incubator (37° C., 5% CO$_2$). Next, the plates were measured on an Infinite reader (Tecan) using an excitation wavelength of 530 nm. The half maximal cytotoxic concentration (CC50) was also determined, defined as the concentration required to reduce the resazurin conversion by 50% compared to that of the cell control wells (Table 1). Finally, the selectivity index (SI) is determined for the compounds, which is calculated as followed: SI=CC$_{50}$/EC$_{50}$.

TABLE 1

EC$_{50}$, CC$_{50}$, and SI for the compounds of the invention in the DENV-2 antiviral assay

| compound# | EC50 (µM) | N | CC50 (µM) | N | SI | N |
|---|---|---|---|---|---|---|
| 1 | 0.0030 | 4 | 6.2 | 4 | 2053 | 4 |
| 1A | 0.00081 | 14 | 4.3 | 16 | 5395 | 13 |
| 1B | 0.14 | 7 | 6.3 | 7 | 44 | 7 |
| 2A | 0.00081 | 4 | 4.2 | 4 | 5166 | 4 |
| 2B | 0.081 | 3 | 6.2 | 3 | 77 | 3 |
| 3 | 0.00072 | 3 | 5.5 | 3 | 7587 | 3 |
| 3A | 0.00034 | 4 | 4.5 | 4 | 20070 | 4 |
| 3B | 0.045 | 3 | 7.1 | 3 | 158 | 3 |
| 4 | 0.0014 | 3 | 6.3 | 4 | 4398 | 3 |
| 4A | 0.00070 | 3 | 4.9 | 3 | 6965 | 3 |
| 4B | 0.045 | 3 | 7.4 | 3 | 164 | 3 |
| 5 | 0.0023 | 3 | 6.5 | 3 | 2860 | 3 |
| 5A | 0.00084 | 4 | 5.9 | 4 | 7057 | 4 |
| 5B | 0.40 | 3 | 8.1 | 3 | 21 | 3 |
| 6 | 0.0012 | 3 | 5.6 | 3 | 4639 | 3 |
| 6A | 0.00082 | 15 | 5.1 | 15 | 6520 | 14 |
| 6B | 0.076 | 4 | 5.4 | 4 | 71 | 4 |
| 7 | 0.0026 | 3 | 7.4 | 3 | 2860 | 3 |
| 7A | 0.0011 | 4 | 6.1 | 4 | 5569 | 4 |
| 7B | 0.069 | 3 | 7.8 | 3 | 112 | 3 |
| 8 | 0.0024 | 3 | 8.0 | 3 | 3270 | 3 |
| 8A | 0.0012 | 3 | 4.2 | 3 | 3457 | 3 |
| 8B | 0.26 | 3 | 5.7 | 3 | 22 | 3 |
| 9 | 0.0022 | 3 | 7.3 | 3 | 3329 | 3 |
| 9A | 0.0044 | 4 | 3.9 | 4 | 899 | 4 |
| 9A | 0.076 | 3 | 6.5 | 3 | 85 | 3 |
| 10 | 0.0075 | 3 | 5.8 | 3 | 767 | 3 |
| 10A | 0.0032 | 3 | 4.5 | 3 | 1416 | 3 |
| 10B | 0.19 | 4 | 3.8 | 3 | 20 | 3 |
| 11 | 0.0031 | 3 | 5.8 | 3 | 1879 | 3 |
| 11A | 0.090 | 3 | 6.5 | 3 | 72 | 3 |
| 11B | 0.0012 | 3 | 4.1 | 3 | 3526 | 3 |

N = the number of independent experiments in which the compounds were tested.

Tetravalent Reverse Transcriptase Quantitative-PCR (RT-qPCR) Assay: Protocol A.

The antiviral activity of the compounds of the invention was tested against DENV-1 strain TC974#666 (NCPV), DENV-2 strain 16681, DENV-3 strain H87 (NCPV) and DENV-4 strains H241 (NCPV) and EDEN (SG/06K2270DK1/2005; GenBank accession number QG398256) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; table 2) and a cellular reference gene (β-actin, table 2). Subsequently, a duplex real time PCR was performed on a Lightcycler480 instrument. The generated Cp value is inversely proportional to the amount of RNA expression of these targets. Inhibition of DENV replication by a test compound result in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin). In addition, $CC_{50}$ values were determined based on the Cp values acquired for the housekeeping gene β-actin.

Biosystems). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined (Tables 6-9).

TABLE 2

Primers and probes used for the real-time, quantitative RT-PCR.

| Primer/probe | Target | Sequence[a,b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | *FAM*-5'-AAGGACTAGAGGTTAGAGGAGACCCCCC-3'-*BHQ1* |
| Factin743 | β-actin | 5'-GGCCAGGTCATCACCATT-3' |
| Ractin876 | β-actin | 5'-ATGTCCACGTCACACTTCATG-3' |
| Pactin773 | β-actin | *HEX*-5'-TTCCGCTGCCCTGAGGCTCTC-3'-*BHQ1* |

[a] Reporter dyes (FAM, HEX) and quencher (BHQ1) elements are indicated in bold and italics.
[b] The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 4-fold serial dilution of 9 dilution steps of the test compound at 200 times the final concentration in 100% DMSO (500 nL; final concentration range: 25 μM-0.00038 μM). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Then, DENV-1 strain TC974#666, DENV-2 strain 16681, DENV-3 strain H87 or DENV-4 strains H241 or EDEN were added. Therefore, 25 μL of virus suspension, where a Cp of ~22 was achieved in RTqPCR, was added to all the wells containing test compound and to the wells assigned as virus control. In parallel, 25 μL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacture's guideline (Applied

TABLE 3 cDNA synthesis using Mix A, denaturation, Mix B and reverse transcription.

| A Mix A | | | | | |
|---|---|---|---|---|---|
| Plates 8 | | | | Reaction Vol. (μl) 20 | |
| Samples 828 | | Concentration | | Volume for (μl) | |
| Mix Item | Unit | Stock | Final | 1 sample | x samples |
| Milli-Q $H_2O$ | | | | 7.27 | 6019.56 |
| R3utr425 | μM | 20 | 0.27 | 0.15 | 124.20 |
| Ractin876 | μM | 20 | 0.27 | 0.15 | 124.20 |
| | | Volume mix/well (μl) | | 7.57 | |
| | | Cell lysates | | 5.00 | |

| B Denaturation step: | | |
|---|---|---|
| Step | Temp | Time |
| Denaturation | 75° C. | 5' |
| Hold | 4° C. | hold |

TABLE 3-continued cDNA synthesis using Mix A, denaturation, Mix B and reverse transcription.

C Mix B

Samples 864

| Mix Item | Unit | Concentration Stock | Final | Volume for (µl) 1 sample | x samples |
|---|---|---|---|---|---|
| Expand HIFI buffer 2 | X | 10.00 | 1.00 | 2.00 | 1728.0 |
| MgCl$_2$ | mM | 25.00 | 3.50 | 2.80 | 2419.2 |
| dNTPs | mM | 10.00 | 1.00 | 2.00 | 1728.0 |
| Rnase inhibitor | U/µl | 40.00 | 1.00 | 0.50 | 432.0 |
| Expand RT | U/µl | 50.00 | 0.33 | 0.13 | 112.3 |
| Total Volume Mix (µl) | | | | 7.43 | |

D Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A Mix C

Samples 833

| Mix Item | Unit | Concentration Stock | Final | Reaction Vol. (µl) 25 Volume for (µl) 1 sample | x samples |
|---|---|---|---|---|---|
| H$_2$O PCR grade Roche | | | | 7.74 | 6447.42 |
| Roche 2xMM mix | X | 2 | 1 | 12.50 | 10412.50 |
| F3utr258 | µM | 20 | 0.3 | 0.38 | 316.54 |
| R3utr425 | µM | 20 | 0.3 | 0.38 | 316.54 |
| P3utr343 | µM | 20 | 0.1 | 0.13 | 108.29 |
| Factin743 | µM | 20 | 0.3 | 0.38 | 316.54 |
| Ractin876 | µM | 20 | 0.3 | 0.38 | 316.54 |
| Pactin773 | µM | 20 | 0.1 | 0.13 | 108.29 |
| Volume Mix/Tube (µl) | | | | 22.02 | |
| cDNA | | | | 3.00 | |

B Protocol qPCR3

| Step | Temp | Time | Ramp rate | | |
|---|---|---|---|---|---|
| preincub/denat | 95° C. | 10 min | 4.4 | | |
| Denaturation | 95° C. | 10 sec | 4.4 | | |
| annealing | 58° C. | 1 min | 2.2 | 40 cycles |
| Elongation | 72° C. | 1 sec | 4.4 | |
| Cooling | 40° C. | 10 sec | 1.5 | |

Tetravalent Quantitative Reverse Transcriptase-PCR (RT-qPCR) Assay: Protocol B.

Vero cells (4×10$^4$) were seeded in 96-well plates. After one day, cell culture medium was replaced with 100 µL assay medium containing a 2×, 3× or 5× serial dilution of the compound (concentration range: 50 µg/mL-0.00038 µg/mL, 50 µg/mL-0.0076 µg/mL, and 50 µg/mL-0.00013 µg/mL, respectively) and 100 µL of dengue virus dilution, where a Ct of ~20 is achieved in RTqPCR. Following a 2 hour incubation period, the cell monolayer was washed 3 times with assay medium to remove residual, non-adsorbed virus and cultures were further incubated for either 4 days (DENV-2 NGC-Tongalike) or 7 days (DENV-1 Djibouti strain D1/H/IMTSSA/98/606, DENV-3 strain H87 prototype, DENV-4 strain H241) in the presence of the inhibitor. Supernatant was harvested and viral RNA load was determined by real-time quantitative RT-PCR. The 50% effective concentration ($EC_{50}$), which is defined as the compound concentration that is required to inhibit viral RNA replication by 50%, was determined using logarithmic interpolation (Tables 7 and 8).

RNA was isolated from 100 µL supernatant with the NucleoSpin 96 Virus kit (Filter Service, Düren, Germany) as described by the manufacturer. The sequences of the TaqMan primers (DENV-For, DENV-Rev; Table 5) and TaqMan probes (DENV-Probe Table 5) were selected from non-structural gene 3 (NS3) or NS5, of the respective flaviviruses using Primer Express software (version 2.0; Applied Biosystems, Lennik, Belgium). The TaqMan probe was fluorescently labelled with 6-carboxyfluorescein (FAM) at the 5' end as the reporter dye, and with minor groove binder (MGB) at the 3' end as the quencher (Table 5). One-step, quantitative RT-PCR was performed in a total volume of 25 µL, containing 13.9375 µL H$_2$O, 6.25 µL master mix (Eurogentec, Seraing, Belgium), 0.375 µL forward primer, 0.375 µL reverse primer, 1 µL probe, 0.0625 µL reverse transcriptase (Eurogentec) and 3 µL sample. RT-PCR was performed using the ABI 7500 Fast Real-Time PCR System (Applied Biosystems, Branchburg, N.J., USA) using the following conditions: 30 min at 48° C. and 10 min at 95° C., followed by 40 cycles of 15 s at 95° C. and 1 min at 60° C. The data was analyzed using the ABI PRISM 7500 SDS software (version 1.3.1; Applied Biosystems). For absolute quantification, standard curves were generated using 10-fold dilutions of template preparations of known concentrations.

TABLE 5

Primers and probes used for real-time, quantitative RT-PCR.

| Primer/Probe | Sequence (5' → 3')[a] | Source[b] | Target |
|---|---|---|---|
| DENV-For | TCGGAGCCGGAGTTTACAAA (SEQ ID N. 1) | DENV2 NGC | NS3 |
| DENV-Rev | TCTTAACGTCCGCCCATGAT (SEQ ID N. 2) | | |
| DENV-Probe | FAM-ATTCCACACAATGTGGCAT-MGB (SEQ ID N. 3) | | |

TABLE 5-continued

Primers and probes used for real-time, quantitative RT-PCR.

| Primer/Probe | Sequence (5' → 3')[a] | Source[b] | Target |
|---|---|---|---|
| DenS | GGATAGACCAGAGATCCTGCTGT (SEQ ID N. 4) | | DENV-1, -3, -4 NS5 |
| DenAS1-3 | CATTCCATTTTCTGGCGTTC (SEQ ID N. 5) | | DENV-1, -3 |
| DenAS4 | CAATCCATCTTGCGGCGCTC (SEQ ID N. 6) | | DENV-4 |
| DEN_1-3 probe | _FAM_-CAGCATCATTCCAGGCACAG-_MGB_ (SEQ ID N. 7) | | DENV-1, -3 |
| DEN_4 probe | _FAM_-CAACATCAATCCAGGCACAG-_MGB_ (SEQ ID N. 8) | | DENV-4 |

[a]Reporter dye (FAM) and quencher (MGB/TAMRA) elements are indicated in bold and italics.
[b]The nucleotide sequence and position of the primers and probes within the genome were deduced from the nucleotide sequence of DENV 2 NGC (GenBank accession no. M29095; Irie et al., 1989), dengue virus serotype 1 Djibouti strain D1/H/IMTSSA/98/606 (Genbank Accession Number AF298808), dengue virus serotype 3 strain H87 prototype (c93130), dengue virus serotype 4 strain H241 (no sequences available).

Cytotoxic Assay (Protocol B)

Potential cytotoxic effects of the compounds were evaluated in uninfected Vero cells. Cells were seeded at $4 \times 10^4$ cells/well in a 96-well plate in the presence of two-, three- or five-fold serial dilutions (ranging from 50 μg/mL-0.0038 μg/mL, 50 μg/mL-0.0076 μg/mL, and 50 μg/mL-0.00013 μg/mL, respectively) of compound and incubated for 4 to 7 days. Culture medium was discarded and 100 μL 3-(4,5-dimethylthiazol-2-yl)-5-(3-carboxymethoxyphenyl)-2-(4-sulfophenyl)-2H-tetrazolium/phenazinemethosulfate (MTS/PMS; Promega, Leiden, The Netherlands) in PBS was added to each well. Following a 2-hour incubation period at 37° C., the optical density was determined at 498 nm. Cytotoxic activity was calculated using the following formula: % cell viability=100×($OD_{Compound}$/$OD_{CC}$), where $OD_{Compound}$ and $OD_{CC}$ correspond to the optical density at 498 nm of the uninfected cell cultures treated with compound and that of uninfected, untreated cell cultures, respectively. The 50% cytotoxic concentration (i.e., the concentration that reduces the total cell number with 50%; $CC_{50}$) was calculated using linear interpolation (Tables 7 and 8).

TABLE 6

$EC_{50}$, $CC_{50}$, and SI for the compounds against serotype 1 in the RT-qPCR assays

| | Protocol A RT-qPCR serotype 1 TC974#666 | | | | | |
|---|---|---|---|---|---|---|
| compound# | EC50 (μM) | N | CC50 (μM) | N | SI | N |
| 1A | 0.0077 | 5 | 4.1 | 5 | 530 | 5 |
| 2A | 0.0071 | 4 | 4.5 | 4 | 628 | 4 |
| 3A | 0.0053 | 3 | 3.8 | 3 | 721 | 3 |
| 4A | 0.0078 | 4 | 4.6 | 3 | 447 | 3 |
| 5A | 0.013 | 3 | 5.2 | 3 | 392 | 3 |
| 6A | 0.0036 | 5 | 4.8 | 5 | 1348 | 5 |
| 7A | 0.016 | 3 | 4.6 | 3 | 282 | 3 |
| 8A | 0.0096 | 3 | 3.5 | 3 | 368 | 3 |
| 9A | 0.0050 | 3 | 4.7 | 3 | 934 | 3 |
| 10A | 0.014 | 3 | 4.1 | 3 | 290 | 3 |
| 11B | 0.018 | 3 | 3.7 | 3 | 202 | 3 |
| | Protocol B RT-qPCR serotype 1 Djibouti | | | | | |
| compound# | EC50 (μM) | N | CC50 (μM) | N | SI | N |
| 1A | 0.022 | 3 | 9.7 | 9 | 506 | 2 |
| 2A | 0.017 | 2 | 7.4 | 5 | 447 | 2 |
| 3A | 0.018 | 2 | 7.7 | 5 | 450 | 2 |
| 4A | 0.020 | 2 | 9.5 | 5 | 392 | 2 |
| 5A | 0.019 | 2 | 7.8 | 5 | 471 | 2 |
| 6A | <0.015 | 3 | 8.1 | 7 | >693 | 3 |
| 7A | 0.020 | 2 | 7.2 | 5 | 366 | 2 |
| 8A | 0.017 | 2 | 7.7 | 5 | 450 | 2 |
| 9A | 0.019 | 2 | 7.9 | 5 | 454 | 2 |
| 10A | 0.020 | 2 | 8.0 | 5 | 413 | 2 |
| 11B | 0.025 | 2 | 7.7 | 5 | 320 | 2 |

N = the number of independent experiments in which the compounds were tested.

TABLE 7

$EC_{50}$, $CC_{50}$, and SI for the compounds against serotype 2 in the RT-qPCR assays

| | Protocol A RT-qPCR serotype 2 16681 | | | | | |
|---|---|---|---|---|---|---|
| compound# | EC50 (μM) | N | CC50 (μM) | N | SI | N |
| 1A | 0.0011 | 9 | 4.7 | 9 | 4457 | 9 |
| 2A | 0.00085 | 4 | 5.7 | 4 | 6744 | 4 |
| 3A | 0.00024 | 3 | 4.3 | 6 | 25632 | 3 |
| 4A | 0.00044 | 5 | 5.2 | 6 | 12915 | 5 |
| 5A | 0.00050 | 4 | 4.5 | 5 | 10575 | 4 |
| 6A | 0.00054 | 7 | 3.7 | 7 | 8391 | 6 |
| 7A | 0.00091 | 3 | 4.7 | 4 | 5763 | 3 |
| 8A | 0.0012 | 3 | 5.2 | 3 | 4406 | 3 |
| 9A | 0.00079 | 3 | 3.8 | 3 | 4833 | 3 |

TABLE 7-continued

EC$_{50}$, CC$_{50}$, and SI for the compounds against serotype 2 in the RT-qPCR assays

| | | | | | | |
|---|---|---|---|---|---|---|
| 10A | 0.0032 | 3 | 4.2 | 3 | 1312 | 3 |
| 11B | 0.0010 | 3 | 4.7 | 3 | 4562 | 3 |

Protocol B
RT-qPCR serotype 2 NGC-Tongalike

| compound# | EC50 (μM) | N | CC50 (μM) | N | SI | N |
|---|---|---|---|---|---|---|
| 1A | 0.00038 | 5 | 14 | 6 | 36900 | 5 |
| 2A | 0.00040 | 3 | 13 | 3 | 31100 | 3 |
| 3A | <0.00033 | 3 | 12 | 3 | >37200 | 3 |
| 4A | <0.00034 | 3 | 13 | 3 | >37300 | 3 |
| 5A | <0.00040 | 3 | 11 | 3 | >28000 | 3 |
| 6A | 0.00040 | 4 | 13 | 4 | 29300 | 3 |
| 7A | 0.00027 | 3 | 12 | 2 | 18900 | 2 |
| 8A | 0.0014 | 3 | 11 | 3 | 8050 | 3 |
| 9A | <0.00031 | 3 | 12 | 3 | >37300 | 3 |
| 10A | 0.0014 | 3 | 12 | 3 | 8910 | 3 |
| 11B | 0.00027 | 3 | 11 | 3 | 37900 | 1 |

N = the number of independent experiments in which the compounds were tested.

TABLE 8

EC$_{50}$, CC$_{50}$, and SI for the compounds against serotype 3 in the RT-qPCR assays Protocol A
RT-qPCR serotype 3 H87

| compound# | EC50 (μM) | N | CC50 (μM) | N | SI | N |
|---|---|---|---|---|---|---|
| 1A | 0.063 | 5 | 1.7 | 4 | 28 | 4 |
| 2A | 0.053 | 4 | 3.9 | 3 | 76 | 3 |
| 3A | 0.036 | 3 | 3.7 | 3 | 104 | 3 |
| 4A | 0.065 | 4 | 3.8 | 2 | 52 | 2 |
| 5A | 0.068 | 3 | 2.9 | 3 | 42 | 3 |
| 6A | 0.026 | 5 | 3.0 | 4 | 106 | 4 |
| 7A | 0.070 | 3 | 4.6 | 2 | 66 | 2 |
| 8A | 0.076 | 3 | 3.6 | 3 | 47 | 3 |
| 9A | 0.063 | 3 | 3.0 | 3 | 48 | 3 |
| 10A | 0.070 | 3 | 3.3 | 3 | 47 | 3 |
| 11B | 0.070 | 3 | 3.4 | 3 | 48 | 3 |

Protocol B
RT-qPCR serotype 3 H87

| compound# | EC50 (μM) | N | CC50 (μM) | N | SI | N |
|---|---|---|---|---|---|---|
| 1A | <0.015 | 6 | 9.7 | 9 | >1440 | 6 |
| 2A | 0.021 | 3 | 7.4 | 5 | 350 | 3 |

TABLE 8-continued

EC$_{50}$, CC$_{50}$, and SI for the compounds against serotype 3 in the RT-qPCR assays

| | | | | | | |
|---|---|---|---|---|---|---|
| 3A | 0.020 | 3 | 7.7 | 5 | 383 | 3 |
| 4A | 0.029 | 3 | 9.5 | 5 | 376 | 3 |
| 5A | 0.025 | 3 | 7.8 | 5 | 291 | 3 |
| 6A | <0.015 | 4 | 8.1 | 7 | >591 | 4 |
| 7A | <0.017 | 3 | 7.2 | 5 | >423 | 3 |
| 8A | 0.032 | 3 | 7.7 | 5 | 244 | 3 |
| 9A | 0.018 | 3 | 7.9 | 5 | 400 | 3 |
| 10A | 0.027 | 3 | 8.0 | 5 | 291 | 3 |
| 11B | 0.026 | 3 | 7.7 | 5 | 294 | 3 |

N = the number of independent experiments in which the compounds were tested.

TABLE 9

EC$_{50}$, CC$_{50}$, and SI for the compounds against serotype 4 strains H241 (A) and SG/06K2270DK1/2005 (B) in the RT-qPCR assays Protocol A
RT-qPCR serotype 4 H241

| compound# | EC50 (μM) | N | CC50 (μM) | N | SI | N |
|---|---|---|---|---|---|---|
| 1A | 0.24 | 10 | 3.1 | 9 | 13 | 9 |
| 2A | 0.26 | 4 | 1.7 | 3 | 7 | 3 |
| 3A | 0.18 | 5 | 3.0 | 5 | 17 | 5 |
| 4A | 0.24 | 4 | 2.4 | 4 | 10 | 4 |
| 5A | 0.32 | 4 | 4.5 | 4 | 13 | 4 |
| 6A | 0.084 | 8 | 2.1 | 8 | 25 | 8 |
| 7A | 0.23 | 3 | 2.8 | 3 | 12 | 3 |
| 8A | 0.30 | 3 | 3.1 | 2 | 11 | 2 |
| 9A | 0.24 | 3 | 2.7 | 3 | 11 | 3 |
| 10A | 0.32 | 3 | 2.7 | 2 | 8 | 2 |
| 11B | 0.35 | 3 | 2.5 | 3 | 7 | 3 |

Protocol A
RT-qPCR serotype 4 EDEN

| compound# | EC50 (μM) | N | CC50 (μM) | N | SI | N |
|---|---|---|---|---|---|---|
| 1A | 0.0062 | 6 | 3.7 | 6 | 583 | 6 |
| 2A | 0.0043 | 5 | 4.4 | 5 | 1007 | 5 |
| 3A | 0.0029 | 4 | 4.1 | 3 | 1579 | 3 |
| 4A | 0.0052 | 5 | 4.4 | 3 | 981 | 3 |
| 5A | 0.0046 | 3 | 4.2 | 2 | 630 | 2 |
| 6A | 0.0029 | 3 | 3.6 | 3 | 1241 | 3 |
| 7A | 0.0066 | 4 | 3.7 | 3 | 536 | 3 |
| 8A | 0.0065 | 4 | 4.5 | 4 | 690 | 4 |
| 9A | 0.0047 | 3 | 2.6 | 3 | 717 | 3 |
| 10A | 0.0086 | 4 | 4.4 | 3 | 436 | 3 |
| 11B | 0.0098 | 4 | 4.0 | 3 | 374 | 3 |

N = the number of independent experiments in which the compounds were tested.

The invention claimed is:

1. A compound of formula (I)

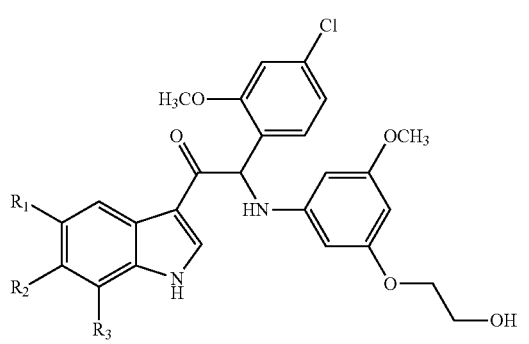

wherein:
when $R_1$ is H, and $R_2$ is F then $R_3$ is H, F or $CH_3$;
when $R_1$ is F or $CH_3$, $R_2$ is $OCH_3$ then $R_3$ is H;
when $R_1$ is F, and $R_2$ is H then $R_3$ is $CH_3$;
when $R_1$ is H, and $R_2$ is $OCH_3$ then $R_3$ is H;
when $R_1$ is H, and $R_2$ is Cl then $R_3$ is H or $CH_3$;
when $R_1$ is F, and $R_2$ is F then $R_3$ is H; and
when $R_1$ is $CH_3$, and $R_2$ is H then $R_3$ is F;
or a stereo-isomeric form, a pharmaceutically acceptable salt, solvate or polymorph thereof.

2. A compound of claim 1 selected from the group consisting of:

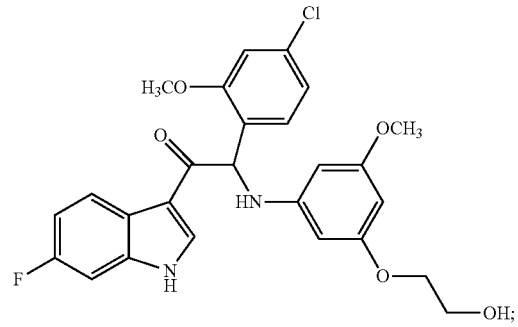

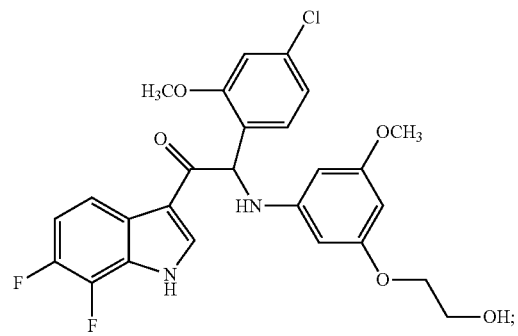

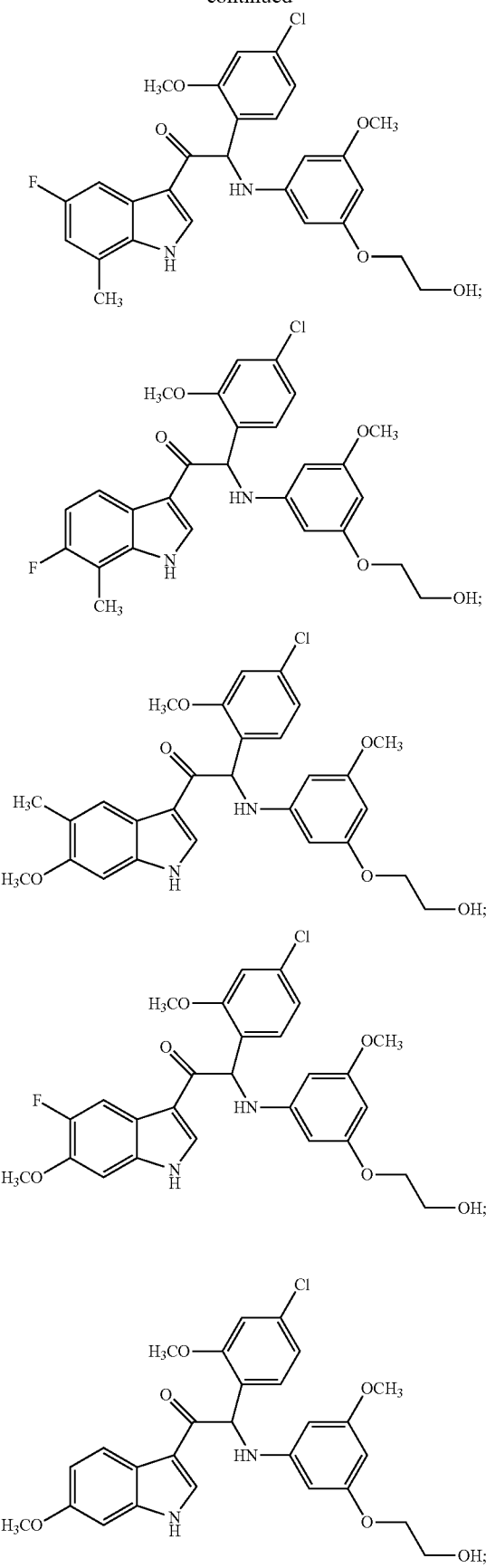
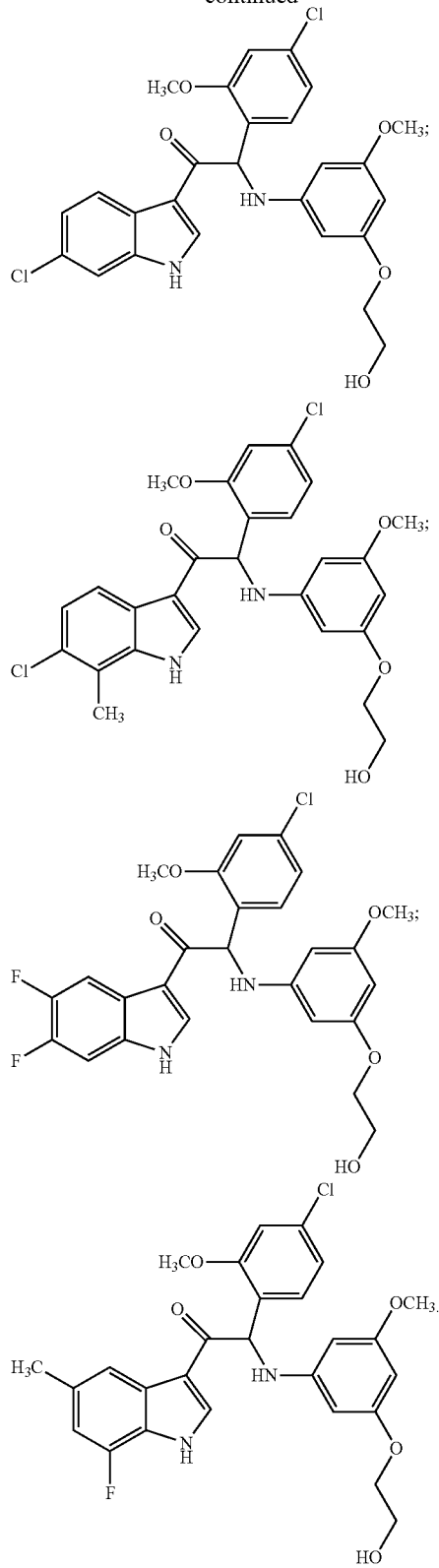
or a stereo-isomeric form, a pharmaceutically acceptable salt, solvate or polymorph thereof.
3. A pharmaceutical composition comprising a compound of formula (I) or a stereo- isomeric form, a pharmaceutically acceptable salt, solvate or polymorph thereof; according to claim 1 and one or more pharmaceutically acceptable excipients, diluents or carriers.

4. A method of treating a dengue viral infection, comprising administering to a mammal a therapeutically effective amount of at least one compound or a stereo-isomeric form, a pharmaceutically acceptable salt, solvate or polymorph thereof as claimed in claim 1.

5. A method of inhibiting the replication of dengue virus in a biological sample or patient, comprising administering to said biological sample or patient a therapeutically effective amount of at least one compound or a stereo-isomeric form, a pharmaceutically acceptable salt, solvate or polymorph thereof as claimed in claim 1.

6. The method as claimed in claim 5 further comprising co-administering an additional therapeutic agent.

7. The method as claimed in claim 6 wherein said additional therapeutic agent is at least one selected from the group consisting of an antiviral agent and a dengue vaccine.

8. A pharmaceutical composition comprising a compound or a stereo-isomeric form, a pharmaceutically acceptable salt, solvate or polymorph thereof according to claim 2 and one or more pharmaceutically acceptable excipients, diluents or carriers.

9. A method of treating a dengue viral infection, comprising administering to a mammal a therapeutically effective amount of at least one compound or a stereo-isomeric form, a pharmaceutically acceptable salt, solvate or polymorph thereof as claimed in claim 2.

10. The compound of claim 2 which is

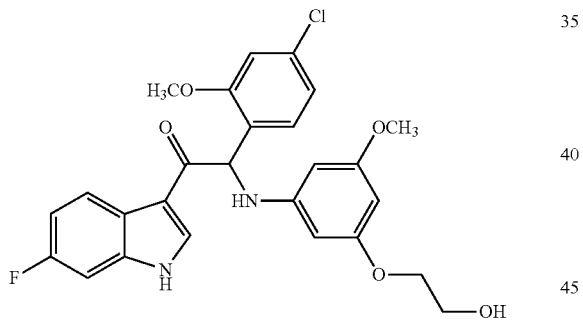

or a stereo-isomeric form, a pharmaceutically acceptable salt, solvate or polymorph thereof.

11. The compound of claim 10, which is

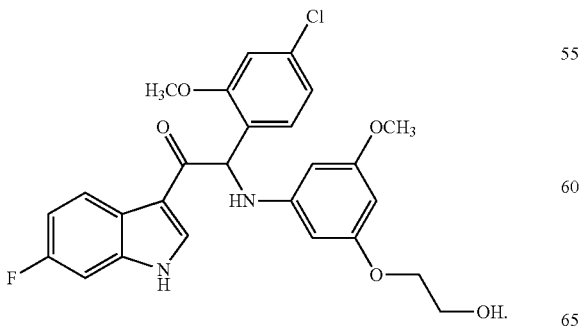

12. The method of claim 4 wherein said compound is

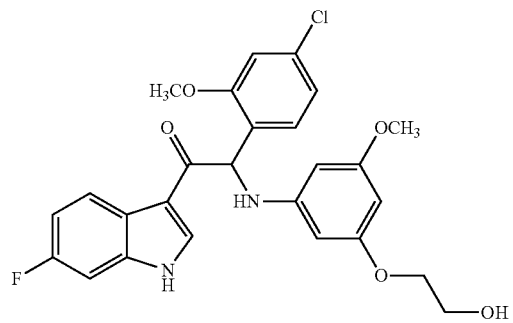 [SMILES: COc1cc(NC(C(=O)c2c[nH]c3cc(F)ccc23)c2ccc(Cl)cc2OC)cc(OCCO)c1]

or a stereo-isomeric form, a pharmaceutically acceptable salt, solvate or polymorph thereof.

13. The method of claim 12, wherein said compound is

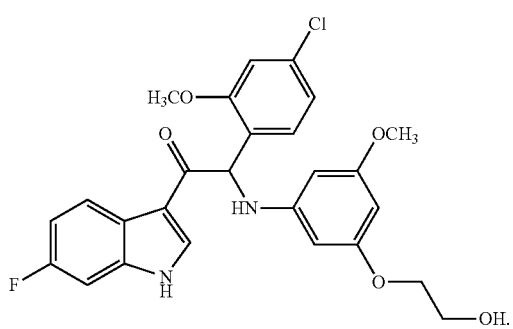 [SMILES: COc1cc(NC(C(=O)c2c[nH]c3cc(F)ccc23)c2ccc(Cl)cc2OC)cc(OCCO)c1]

14. The method of claim 5, wherein said compound is

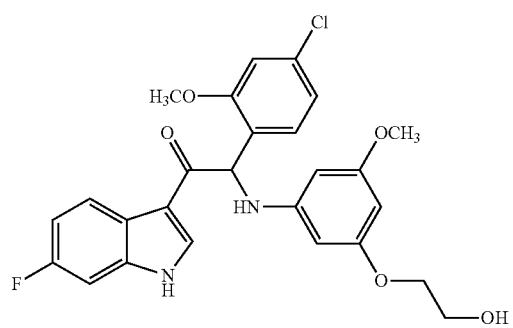 [SMILES: COc1cc(NC(C(=O)c2c[nH]c3cc(F)ccc23)c2ccc(Cl)cc2OC)cc(OCCO)c1]

or a stereo-isomeric form, a pharmaceutically acceptable salt, solvate or polymorph thereof.

15. The method of claim 14, wherein said compound is
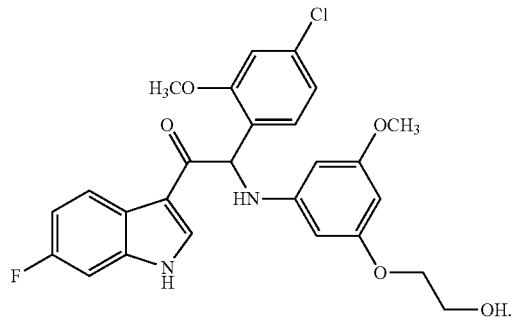 [SMILES: COc1cc(NC(C(=O)c2c[nH]c3cc(F)ccc23)c2ccc(Cl)cc2OC)cc(OCCO)c1]
16. The pharmaceutical composition of claim 8, wherein said compound is
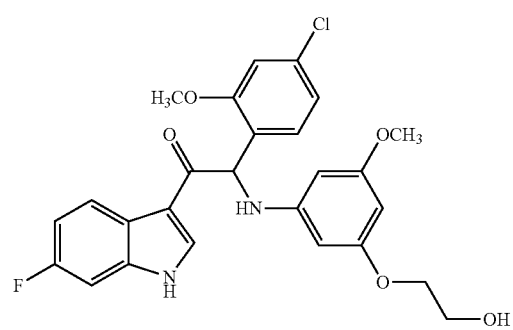 [SMILES: COc1cc(NC(C(=O)c2c[nH]c3cc(F)ccc23)c2ccc(Cl)cc2OC)cc(OCCO)c1]
or a stereo- isomeric form, a pharmaceutically acceptable salt, solvate or polymorph thereof.
17. The pharmaceutical composition of claim 16, wherein said compound is
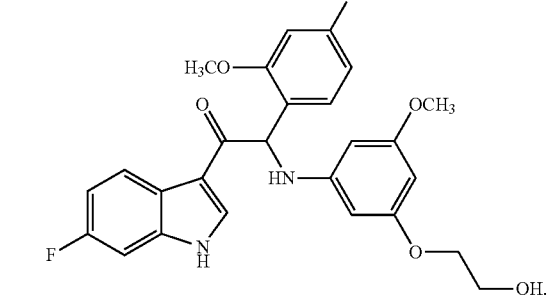
* * * * *